United States Patent
Barker et al.

(10) Patent No.: US 9,679,051 B2
(45) Date of Patent: Jun. 13, 2017

(54) ANSWER SEQUENCE EVALUATION

(71) Applicant: International Business Machines Corporation, Armonk, NY (US)

(72) Inventors: Kevin S. Barker, Raleigh, NC (US); Thomas J. Eggebraaten, Rochester, MN (US); Mark G. Megerian, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/708,510

(22) Filed: May 11, 2015

(65) Prior Publication Data

US 2016/0125750 A1    May 5, 2016

Related U.S. Application Data

(63) Continuation of application No. 14/570,797, filed on Dec. 15, 2014, now Pat. No. 9,501,525.

(Continued)

(51) Int. Cl.
*G09B 3/06* (2006.01)
*G09B 7/00* (2006.01)
(Continued)

(52) U.S. Cl.
CPC ...... *G06F 17/30734* (2013.01); *G06F 17/271* (2013.01); *G06F 17/2705* (2013.01);
(Continued)

(58) Field of Classification Search
None
See application file for complete search history.

(56) References Cited

U.S. PATENT DOCUMENTS

| 4,965,763 A | 10/1990 | Zamora |
| 5,930,746 A | 7/1999 | Ting |

(Continued)

FOREIGN PATENT DOCUMENTS

| GB | 2468203 A | 9/2010 |
| WO | 2005017656 A2 | 2/2005 |

(Continued)

OTHER PUBLICATIONS

Jijkoun et al. (Jijkoun04), Answer Selection in a Multi-Stream Open Domain Question Answering System [online], 2004, [retrieved on Feb. 7, 2016]. Retrieved from the Internet:<URL:https://www.google.com/url?sa=t&rct=j&q=&esrc=s&source=web&cd=1&ved=0ahUKEwjKnvmZyOfKAhUX3WMKHZZ9AQoQFggfMAA&url=https%3A%2F%2Fstaff.fnwi.uva.nl%2Fm.derijke>.*

(Continued)

*Primary Examiner* — Lut Wong
*Assistant Examiner* — Nathan Brown, Jr.
(74) *Attorney, Agent, or Firm* — Nicholas D. Bowman

(57) ABSTRACT

Aspects of the present disclosure are directed toward evaluating an answer sequence. Aspects are directed toward receiving a set of answer sequences including a first answer sequence. The first answer sequence may have a first set of answers. Aspects are also directed toward identifying a set of scores coupled with the first set of answers. Aspects are also directed toward determining, based on a subject matter corresponding to the first answer sequence, a set of evaluation rules. Aspects are also directed toward generating, based on the set of scores and the set of evaluation rules, a sequence evaluation score for the first answer sequence.

3 Claims, 19 Drawing Sheets

Related U.S. Application Data

(60) Provisional application No. 62/075,635, filed on Nov. 5, 2014.

(51) Int. Cl.

| | | |
|---|---|---|
| *G09B 7/06* | (2006.01) | |
| *G06F 17/30* | (2006.01) | |
| *G06F 17/27* | (2006.01) | |
| *G06F 17/28* | (2006.01) | |
| *G06F 19/00* | (2011.01) | |
| *G06N 5/02* | (2006.01) | |
| *G06N 5/04* | (2006.01) | |
| *G06N 7/00* | (2006.01) | |
| *G06N 99/00* | (2010.01) | |
| *G06Q 30/02* | (2012.01) | |
| *G09B 7/02* | (2006.01) | |

(52) U.S. Cl.
CPC ........ *G06F 17/277* (2013.01); *G06F 17/2785* (2013.01); *G06F 17/28* (2013.01); *G06F 17/3043* (2013.01); *G06F 17/3053* (2013.01); *G06F 17/3097* (2013.01); *G06F 17/30528* (2013.01); *G06F 17/30595* (2013.01); *G06F 17/30598* (2013.01); *G06F 17/30663* (2013.01); *G06F 17/30864* (2013.01); *G06F 17/30867* (2013.01); *G06F 17/30876* (2013.01); *G06F 19/325* (2013.01); *G06F 19/363* (2013.01); *G06N 5/022* (2013.01); *G06N 5/046* (2013.01); *G06N 7/005* (2013.01); *G06N 99/005* (2013.01); *G06Q 30/0203* (2013.01); *G09B 7/00* (2013.01); *G09B 7/02* (2013.01)

(56) References Cited

U.S. PATENT DOCUMENTS

| | | | |
|---|---|---|---|
| 7,542,894 B2 | 6/2009 | Murata | |
| 7,953,720 B1 | 5/2011 | Rohde et al. | |
| 8,055,603 B2 | 11/2011 | Angell et al. | |
| 8,280,885 B2 | 10/2012 | Cardie et al. | |
| 8,370,278 B2 | 2/2013 | Vadlamani et al. | |
| 8,417,514 B2 | 4/2013 | Brown et al. | |
| 8,438,054 B2 | 5/2013 | Lowrance et al. | |
| 8,443,189 B2 | 5/2013 | Li et al. | |
| 8,539,404 B2 | 9/2013 | Craig et al. | |
| 8,601,030 B2 | 12/2013 | Bagchi et al. | |
| 8,819,007 B2 | 8/2014 | Brown et al. | |
| 8,832,064 B2 | 9/2014 | Stenchikova et al. | |
| 2005/0010444 A1 | 1/2005 | Iliff | |
| 2007/0172808 A1 | 7/2007 | Capone | |
| 2008/0104065 A1 | 5/2008 | Agarwal et al. | |
| 2008/0154581 A1 | 6/2008 | Lavi et al. | |
| 2008/0221923 A1 | 9/2008 | Shogan | |
| 2009/0007924 A1 | 1/2009 | Iliff | |
| 2010/0049679 A1 | 2/2010 | Phillips | |
| 2011/0029946 A1 | 2/2011 | Joukov et al. | |
| 2011/0125734 A1 | 5/2011 | Duboue et al. | |
| 2012/0102193 A1 | 4/2012 | Rathore et al. | |
| 2012/0311025 A1 | 12/2012 | Garcia Aranda | |
| 2012/0331391 A1 | 12/2012 | Kanjirathinkal et al. | |
| 2013/0114694 A1 | 5/2013 | Chen et al. | |
| 2013/0117024 A1 | 5/2013 | Glass et al. | |
| 2013/0262501 A1 | 10/2013 | Kuchmann-Beauger et al. | |
| 2014/0006106 A1 | 1/2014 | Malov et al. | |
| 2014/0019443 A1 | 1/2014 | Golshan | |
| 2014/0032277 A1 | 1/2014 | Kashyap | |
| 2014/0164303 A1 | 6/2014 | Bagchi et al. | |
| 2014/0188462 A1 | 7/2014 | Zadeh | |
| 2014/0201126 A1 | 7/2014 | Zadeh et al. | |
| 2014/0229161 A1 | 8/2014 | Gliozzo | |
| 2014/0229163 A1 | 8/2014 | Gliozzo | |
| 2014/0272909 A1 | 9/2014 | Isensee et al. | |
| 2014/0337329 A1 | 11/2014 | Brown et al. | |

FOREIGN PATENT DOCUMENTS

| | | |
|---|---|---|
| WO | 2009007686 A1 | 1/2009 |
| WO | 2012122196 A2 | 9/2012 |

OTHER PUBLICATIONS

Matsuda et al. (MATSUDA05), Synthesis of Multiple Answer Evaluation Measures using a Machine Learning Technique for a QA System Proceedings of NTCIR-5 Workshop Meeting Tokyo, Japan [online], Dec. 6-9, 2005, [retrieved on Feb. 7, 2016]. Retrieved from the Internet<URL:http://citeseerx.ist.psu.edu/download;doi=10.1.1.468.4356&rep=rep1&typ=pdf>.*

Chen et al., "An RNN-Based Prosodic Information Synthesizer for Mandarin Text-to-Speech", IEEE Transactions on Speech and Audio Processing, vol. 6, No. 3, 1998, pp. 226-239, © 1998 IEEE.

Chen, W., "Parameterized Spatial SQL Translation for Geographic Question Answering", 2014 IEEE International Conference on Semantic Computing (ICSC), Jun. 2014, pp. 23-27. DOI: 10.1109/ICS.2014.44.

Figueroa et al., "Category-specific Models for Ranking Effective Paraphrases in Community Question Answering", Preprint submitted to Elsevier, Feb. 12, 2014, 26 pages (Subsequently published in Expert Systems With Applications, vol. 41, Issue 10, 2014, 10.1016/j.eswa.2014.02.004).

High et al., "Expert Cancer Care May Soon Be Everywhere, Thanks to Watson", MIND Guest Blog, Scientific American, Oct. 20, 2014, 12 pages. http://blogs.scientificamerican.com/mind-guest-blog/2014/10/20/expert-cancer-care-may-soon-be-everywhere-thanks-to-watson/.

Hovy et al., "A Question/Answer Typology with Surface Text Patterns", Proceedings of HLT 2002, Second International Conference on Human Language Technology Research, 2002, pp. 247-251, Morgan Kaufmann Publishers Inc © 2002.

Li et al., "Graph-based Answer Passage Ranking for Question Answering", 2010 International Conference on Computational Intelligence and Security (CIS), Dec. 2010, pp. 634-638, © 2010 IEEE. DOI: 10.1109/CIS.2010.144.

Wu et al., Personalized Intelligent Question Answering Algorithm in E-Learning, Proceedings of the Fourth International Conference on Machine Learning and Cybernetics, Guangzhou, Aug. 2005, vol. 6, pp. 3299-3303, © 2005 IEEE. DOI: 10.1109/ICMLC.2005.1527512.

Zhou et al., "Group Non-negative Matrix Factorization with Natural Categories for Question Retrieval in Community Question Answer Archives", Proceedings of COLING 2014, the 25th International Conference on Computational Linguistics: Technical Papers, pp. 89-98, Ireland, Aug. 2014.

Zou, X., "Design, Implementation of the Parallel C Language Based on C/S Mode in Distributed Systems", 2011 International Conference on Transportation, Mechanical, and Electrical Engineering (TMEE), Dec. 2011, pp. 532-535, © 2011 IEEE. DOI: 10.1109/TMEE.2011.6199258.

Barker et al., "Parameter Management in a Question-Answering Environment", U.S. Appl. No. 62/075,635, filed Nov. 5, 2014.

Barker et al., "Answer Category Data Classifying Using Dynamic Thresholds", U.S. Appl. No. 14/570,436, filed Dec. 15, 2014.

Barker et al., "Answer Category Data Classifying Using Dynamic Thresholds", U.S. Appl. No. 14/708,536, filed May 11, 2015.

Barker et al., "Answer Management in a Question-Answering Environment", U.S. Appl. No. 14/570,491, filed Dec. 15, 2014.

Barker et al., "Answer Management in a Question-Answering Environment", U.S. Appl. No. 14/708,452, filed May 11, 2015.

Eggebraaten et al., "Answer Interactions in a Question-Answering Environment", U.S. Appl. No. 14/570,456, filed Dec. 15, 2014.

Eggebraaten et al., "Answer Interactions in a Question-Answering Environment", U.S. Appl. No. 14/708,689, filed May 11, 2015.

(56) References Cited

OTHER PUBLICATIONS

Barker et al., "Answer Sequence Discovery and Generation", U.S. Appl. No. 14/570,683, filed Dec. 15, 2014.
Barker et al., "Answer Sequence Discovery and Generation", U.S. Appl. No. 14/663,988, filed Mar. 20, 2015.
Barker et al., "Answer Sequence Evaluation", U.S. Appl. No. 14/570,797, filed Dec. 15, 2014.
List of IBM Patents or Patent Applications Treated as Related.
Cairns et al., "The MiPACQ Clinical Question Answering System", AMIA Annual Symposium Proceedings 2011, Epub Oct. 22, 2011, 10 pages.

\* cited by examiner

| Treatment Plans For Cancer Treatment 100 | | | |
|---|---|---|---|
| Answer Category (Chemotherapy) 102 | Answer Category (Surgery) 104 | Answer Category (Endocrine) 106 | Answer Category (Radiation) 108 |
| Treatment Answer (Chemotherapy A) 110 | Treatment Answer (Surgery A) 112 | Treatment Answer (Endocrine A) 114 | Treatment Answer (Radiation A) 116 |
| Treatment Answer (Chemotherapy B) 118 | Treatment Answer (Surgery B) 120 | - | Treatment Answer 122 |
| - | Treatment Answer (Surgery C) 124 | Treatment Answer 126 | Treatment Answer 128 |

109 (row 1), 130 (row 2), 132 (row 3), 134 (row 4)

FIG. 1

| 1200 |
|---|

Discovered Answer Sequences — 1202

| 1210 → 1 | Surgery B | Chemotherapy A | Endocrine A | Radiation B |
| 1220 → 2 | Radiation B | Surgery A | Chemotherapy C | Endocrine C |

Generated Answer Sequences — 1222

| 1230 → 3 | Endocrine A | Radiation B | Surgery B | Chemotherapy C |
| 1240 → 4 | Endocrine A | Radiation B | Surgery C | Chemotherapy C |

FIG. 12

ANSWER SEQUENCE EVALUATION

CROSS-REFERENCE TO RELATED APPLICATIONS

This application claims priority from U.S. Provisional Application No. 62/075,635 filed Nov. 5, 2014, entitled "Parameter Management in a Question-Answering Environment," the entirety of which is hereby incorporated herein by reference.

BACKGROUND

The present disclosure relates to answer management in a question-answering (QA) environment and, more specifically, to establishing an answer sequence from the group of answers sorted according to a sequence of answer categories.

Question-answering (QA) systems can be designed to receive input questions, analyze them, and return applicable answers. Using various techniques, QA systems can provide mechanisms for searching corpora (e.g., databases of source items containing relevant content) and analyzing the corpora to determine answers to an input question.

SUMMARY

Aspects of the present disclosure, in certain embodiments, are directed toward receiving a set of answer sequences including a first answer sequence. The answer sequence may have a first set of answers. Aspects also include identifying a set of scores coupled with the first set of answers. Aspects also include determining, based on a subject matter corresponding to the first answer sequence, a set of evaluation rules. Aspects also include generating, based on the set of scores and the set of evaluation rules, a sequence evaluation score for the first answer sequence.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 1 depicts a diagram of an example set of answer sequences, according to embodiments of the present disclosure.

FIG. 12 depicts an example of answer sequence generation, according to embodiments of the present disclosure.

Figure 2:
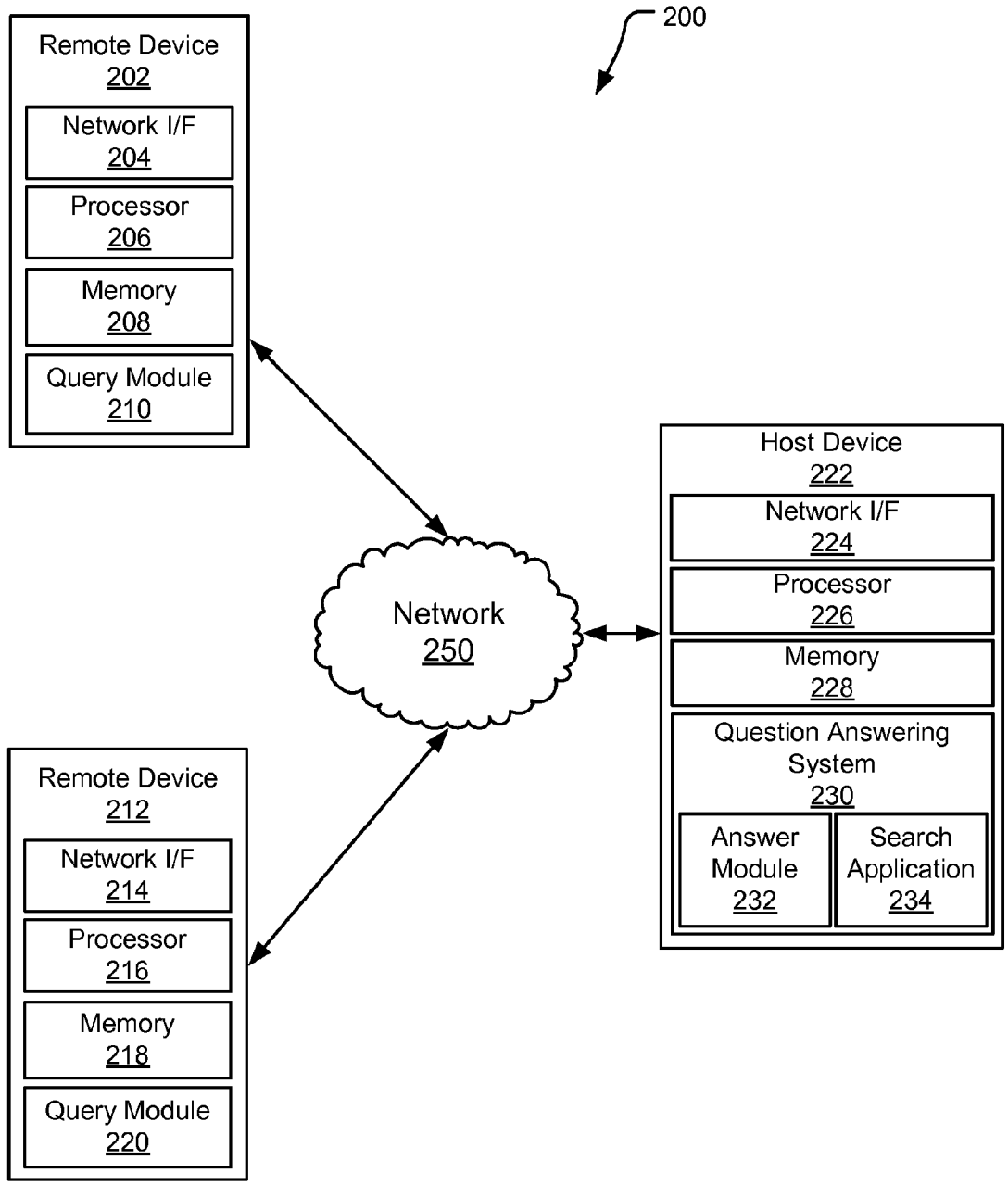
FIG. 2 depicts a block diagram of an example computing environment for use with a question-answering (QA) system, according to embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to answer management in a question-answering (QA) environment, more particular aspects relate to establishing an answer sequence from answers sorted according to a sequence of answer categories. While the present disclosure is not necessarily limited to such applications, various aspects of the disclosure may be appreciated through a discussion of various examples using this context.

Embodiments of the present disclosure are directed towards a system configured for answer management in a QA environment. In a QA system, a group of answers can be generated in response to input queries (e.g., questions). For example, the QA system can be configured to receive an input query, analyze one or more data sources, and based on the analysis, generate the group of answers.

In embodiments, answers can be data generated by a QA system in response to an input query. Answers can be data in various forms including, but not limited to, text, documents, images, video, and audio. In embodiments, answers can be data that suggests an operation or action. For example, the QA system could receive a question asking how to treat a particular medical condition. In response, the QA system could generate a group of answers that collectively suggest a series or group of actions for treating the particular medical condition. For example, the system could analyze a corpus of information and determine that specific medication could be used to treat the particular medical condition. In response, the system could generate an answer indicating that the specific medication should be taken. Described further herein, the QA system can generate answers based on natural language analysis of a corpus of information.

In some instances, the QA system can be further configured to manage organization of the group of answers. In embodiments, the organized group of answers can be outputted to a user as a single, organized, complete answer (e.g., an answer sequence as described herein). In some embodiments, the system can be configured to render a visualization of the organized answer to present the answers to a user. Organizing the set of answers can assist a user in comprehension of the group of answers. In some embodiments, the group of answers can be organized in various forms such as, but not limited to, images, charts, tables, dashboards, maps, and the like.

In some instances, answers from the set of answers can be scored with a confidence value (e.g., a confidence score). The system can be configured to organize of the group of answers by generating an answer list of the group of answers ordered according to the confidence value of each answer. The answer list could then be presented, as an output response, to satisfy the input query.

However, in some instances, the answer list could fail to satisfy the input query. For example, the QA system could receive a question asking how to treat a particular medical condition. In response, the QA system could generate the group of answers that suggest various actions. The system could organize of the group of answers to form an answer list including the various treatments listed according to a confidence score. The answer list could be outputted to a user to attempt to satisfy the input query. In some embodiments, the answers can be treatment answers, where treatment answers are answers that suggest various actions or operations related to medical treatments.

However, the answer list can present answers such that it appears that the highest ranked answers in the list make up the suggested treatment. For example, a user, when seeing the answer list, could think that a single answer (such as the one with the highest confidence score) is the suggested treatment. However, a more desirable response could involve a plurality of treatments. For example, it could be that a combination of two answers, regardless of confidence score, presents a better answer than a single answer. In an additional example, the user, when seeing the answer list, could think that multiple answers (such as the top two answers) make up the suggested treatment, regardless of the category or type of treatment suggested by the multiple answers. However, in some instances, a more desirable response to an input query could involve applying multiple categories or types of treatments. Additionally, a more desirable response could involve applying multiple answers in a particular sequence.

For example, in the field of oncology, a more desirable response to a question of how to treat a specific cancer could generally involve two categories of treatment answers. The categories could include a radiation treatment and a chemotherapy treatment. Additionally in some instances, a more desirable response could include applying the categories in a particular sequence. For example, an answer could include first performing a radiation treatment and then a chemotherapy treatment. Additionally, in some instances, the categories could be applied in an overlapping manner. For example, an answer could include first beginning a radiation treatment and then, prior to completing the radiation treatments, beginning a chemotherapy treatment.

Therefore, in embodiments, the system could be configured to manage the group of answers to organize answers according to a plurality of answer categories. In embodiments, answer categories are classifications that can be applied to the group of answers to assist in organization of the answers.

For example, the answer categories could be used to classify the group of answers according to type of action suggested by each answer. For a group of answers generated in response to a question asking how to troubleshoot a computer, the answer categories could include hardware troubleshooting and software troubleshooting. Described further herein, the answer categories can be determined based on a subject matter of data (such as input queries and the generated answers) in the QA environment.

In embodiments, the system can be configured to sort the group of answers into a plurality of answer categories. For example, the system could sort a first set of the group of answers related to hardware troubleshooting into a first answer category which corresponds to hardware troubleshooting. The system could sort a second set of answers related to software troubleshooting into a second answer category, which corresponds to software troubleshooting.

In some embodiments, the answer categories can be ordered according to a sequence. The sequence of answer categories can be referred to herein as a category sequence. For example, for an answer to an input query related to cancer treatments, a category sequence could include ordered steps of first applying radiation type treatments and then applying chemotherapy type treatments. In an additional example, for an answer to an input query related to computer troubleshooting, a category sequence could include ordered steps of first applying hardware troubleshooting and then software troubleshooting. Described further herein, the category sequences can be determined based on the subject matter of data (such as input queries and the generated answers) in the QA environment.

The system can be configured to establish, based on the one or more category sequences, one or more answer sequences. The one or more answer sequences can be established from answers from one or more answer categories ordered according to the one or more category sequences. For example, a first set of answers could be sorted into a first answer category and a second set of answers could be sorted into a second answer category. A category sequence could include the first answer category followed by the second answer category. Thus, an answer sequence could include a first answer from the first set of answers followed by a second answer from the second set of answers.

In some instances, a QA system could generate an answer sequence and present the answer sequence to a user without properly evaluating the interactions between the answers that form the presented answer sequence. This could lead to improper levels of confidence in the answer sequence (e.g., confidence scores that are too high or too low). For example, in the field of oncology, a QA system could determine a confidence score for a specific oncology treatment plan (answer sequence) without considering how the specific treatments (answers) that make up the treatment plan are likely to interact. This could occur, for example, where a confidence score for a treatment plan is generated as a composite of the confidence scores of each specific treatment of the treatment plan. In such a situation, unless the individual treatments are evaluated in view of their interactions with each other (e.g., where the individual treatments are not scored independently), the composite confidence score for the treatment plan could be inappropriate.

In some instances, a failure to take into account answer interactions could lead to confidence scores that are too high. For example, in the field of IT support, just because a particular computer troubleshooting plan (answer sequence) calls for using the debugger (first answer) with the highest confidence score of all of the debuggers identified in the QA environment followed by using the network analyzer (second answer) with the highest confidence score of all of the network analyzers identified in the QA environment does not mean that that particular computer troubleshooting plan is likely to be the best plan or even that it is likely to be a good plan. There could be known (or at least discoverable) negative interactions between the two answers (the particular debugger and the particular network analyzer) that could be considered before recommending or presenting this particular plan to a user.

In some embodiments of the present disclosure, likely interactions between answers of a particular answer sequence can be considered as part of the ranking and/or scoring answer sequences. In some embodiments, this can involve generating an answer relationship in an answer sequence. Specifically, this can occur by first identifying the answer sequence, which can include at least a first answer and a second answer. Next, a corpus can be analyzed using the first answer and the second answer in order to identify a set of influence factors that correspond to both answers. Based on this set of influence factors, the answer relationship between the first answer and the second answer may be generated.

In some embodiments, an answer sequence may include three or more answers. In such embodiments, answer relationships between each answer of the answer sequence and all of the remaining answers of the answer sequence may be generated by identifying sets of influence factors between each possible answer-answer pairing within the answer sequence. Each set of influence factors may be used to generate a separate answer relationship. In some embodiments, the answer sequence may be evaluated, at least in part, based on the answer relationships between its constituent answers.

In some embodiments, a relationship score may be assigned to each answer relationship based on its set of influence factors. Further, in some embodiments, the one or more relationship scores applied to the answer relationships of a particular answer sequence, may impact the confidence score of the answer sequence. Furthermore, in some embodiments, thresholds may be applied to relationship scores in order to determine if corresponding answer sequences are to be deemed improper, unusable, or otherwise contraindicated.

In some embodiments, identifying a set of influence factors corresponding to both a first answer and a second answer of an answer sequence may involve identifying a direct influence relationship between the first answer and the second answer. Based on the direct influence relationship, at least one influence factor of the set of influence factors can be identified.

In some embodiments, identifying a set of influence factors corresponding to both a first answer and a second answer of an answer sequence may involve identifying a first characteristic relationship between the first answer and a characteristic and a second characteristic relationship between the second answer and the characteristic. The first characteristic relationship and the second characteristic relationship may be compared in order to identify at least one influence factor of the set of influence factors.

In recent years, the increased availability and access to large amounts of content via the Internet, social media, and other networks have resulted in an increase in the need for organizing and managing that content. As described herein, question-answering systems are one tool that can be used to facilitate the ease with which users can find and access desired content. Aspects of the present disclosure, in certain embodiments, relate to the recognition that in certain situations, answers for questions submitted to the question answering system may be part of a larger procedure or sequence of multiple answers (e.g., an answer sequence), and that a single answer may not provide a complete picture of the desired content that the user is seeking. For instance, in the field of oncology, a user searching for the most effective cancer treatment may be overwhelmed by the number of treatment options available, and be unsure of which types of treatments work well with one another or in which order they should be applied. Accordingly, aspects of the present disclosure, in certain embodiments, are directed toward analyzing a corpus of data pertaining to a subject matter (e.g., oncology) and determining an answer sequence for answers identified from the corpus. Further aspects of the present disclosure are directed toward generating an answer sequence model for analyzing known answer sequences and generating additional (e.g., undiscovered) answer sequences. Aspects of the present disclosure may be associated with benefits including content relevance, time saving, and efficiency of content accessibility.

Embodiments of the present disclosure are directed towards a method for managing category specific confidence scores in a QA environment. In embodiments, the method can include sorting, based on a set of answer categories for a subject matter, a first set of a plurality of answers into a first answer category and a second set of the plurality of answers into a second answer category.

In embodiments, each of the first set of the plurality of answers corresponds to at least one of a set of a plurality of confidence scores and each of the second set of the plurality of answers corresponds to at least one of a fourth set of the plurality of confidence scores. In embodiments, the plurality of confidence scores represent confidence of answers to an input query submitted to a QA system. In embodiments, the method can include classifying confidence scores of the third set into one of a plurality of confidence buckets using a first threshold. The method can include determining a fifth set of a plurality of thresholds using the plurality of confidence scores. The method can include classifying unclassified confidence scores of the third set into one of the plurality of confidence buckets using the fifth set of the plurality of thresholds.

As described herein, a QA system can receive an input query and answers to that input query can be generated by the system. In embodiments, the system can be configured to generate corresponding answer confidence scores for one or more of the answers. In some instances, returning the answers and confidence scores alone could overwhelm a user or lead to misinterpretations of the quality of a returned answer, such as in an answer list arrangement, as described herein.

Thus, in some instances, the system can be configured to sort the answers into various answer categories, as described herein. For example, based on a set of answer categories for a subject matter, a first set of a plurality of answers can be sorted into a first answer category and a second set of the plurality of answers into a second answer category. In embodiments, each of the first set of the plurality of answers can correspond to at least one of a third set of a plurality of confidence scores. Similarly, in some embodiments, each of the second set of the plurality of answers can correspond to at least one of a fourth set of the plurality of confidence scores.

Additionally, the system can be configured to classify answers in each of the answer categories into various confidence buckets. The answers in each answer category can be classified based on a confidence score corresponding to each answer. In embodiments, confidence buckets are divisions or classifications for answers based on a value of the answer's confidence score.

For example, the system can be configured to classify the third set of the plurality of confidence scores to one or more confidence buckets. The system could be configured to classify the fourth set of the plurality of confidence scores to one or more confidence buckets.

In embodiments, confidence buckets can contain a group of answers and/or confidence scores and can be associated with one or more threshold values and a descriptive label. For example, answers that have a confidence score above 95 on a scale of 0-100 could be classified into a first bucket labeled "preferred answers". Answers that have a confidence score below 95 could be classified into a second bucket labeled "answers for consideration". Classifying answers into confidence buckets can be beneficial, as the returned answers can be easier to display and interpret. Confidence buckets can be referred to herein as "buckets".

When using buckets, the QA system can determine which answers to associate with which buckets by comparing the answer confidence scores to bucket thresholds. In embodiments, static bucket thresholds can be used to allow answers to be presented according to accepted standards. For instance, an answer confidence above 95 on a scale of 0-100 could attribute high confidence to the corresponding answer. Thus, in some instances, confidence scores greater than 95 would be placed into a high confidence bucket.

However, in some instances, using static bucket thresholds alone could disregard the relative value of a set of answers. For example, if all confidence scores were greater than a static threshold of 95 on a scale of 0-100, the confidence scores could end up classified into a single bucket, such as the preferred answer bucket. A single bucket of answers could only partially indicate or could not indicate relative confidence of answers with respect to other answers.

Thus, in some instances, the system can be configured to use dynamic bucket thresholds based on the answer confidence scores to classify the confidence scores. In embodiments, dynamic bucket thresholds are based on answer confidence scores and the QA system can create bucket thresholds that can capture the relative confidence of the answers. In addition, using both static and dynamic bucket thresholds can allow the system to present answers in a manner that captures relative confidence within a framework of a standard of confidence.

As described herein, in certain situations, answers for questions submitted to the question answering system may be part of a larger procedure or sequence of multiple answers (e.g., an answer sequence), and that a single answer may not provide a complete picture of the desired content that the user is seeking. Often, the answers of the answer sequence may be scored or ranked with confidence values or other quantitative indications of the confidence or reliability of that particular answer.

Aspects of the present disclosure, in certain embodiments, relate to the recognition that it may be desirable to provide an overall composite score (e.g., a sequence evaluation score) for the answer sequence as a whole based on the individual scores of the answers it includes. Furthermore, aspects of the present disclosure relate to the recognition that, depending on the subject matter that the answer sequence pertains to, different methods of generating the sequence evaluation score may be desirable (e.g., answer sequences pertaining to serious subject matters such as oncology, investment plans and the like may be evaluated differently than answer sequences related to entertainment, baking, etc.) Accordingly, aspects of the present disclosure are directed toward determining an evaluation rule for a particular answer sequence based on the subject matter it relates to, as well as other conditions, and generating an overall composite score to indicate the reliability of the answer sequence. Aspects of the present disclosure may be associated with benefits including content relevance, time saving, and efficiency of content accessibility.

Referring now to FIG. 1 a diagram of an example table 100 showing answer sequences can be seen, according to embodiments of the present disclosure. The table 100 can include a plurality of treatment answers 110-128 organized according to various answer categories 102-108. As seen in FIG. 1, the answer categories 102-108 are related to various types of medical treatment categories. For example, answer category 102 is related to chemotherapy, answer category 104 is related to surgery, answer category 106 is related to endocrine therapy, and answer category 108 is related to radiation.

In embodiments, answer categories 102-108 can be referred to as treatment categories. In embodiments, treatment categories are classifications, similar to answer categories, which are applied to treatment answers to assist in organization of treatment answers. For example, treatment answers 110 and 118 are related to chemotherapy treatments and thus are placed in a column underneath the treatment category related to chemotherapy. Similarly, treatment answers 112, 120, and 124 are related to surgery treatments and thus are placed in a column underneath the treatment category related to surgery.

Answer categories 102-108 can be seen arranged in a row 109 in a category sequence. The category sequence is a sequence of answer categories, as described herein. For example, in row 109 the category sequence can include first answer category 102, then answer category 104, then answer category 106 and then answer category 108. In embodiments, a category sequence can be referred to as a treatment template. In embodiments, the treatment template can be the same or substantially similar to the category sequence. In some embodiments, treatment templates can be a specific category sequence that has been identified as acceptable or possible, either by an expert or by the QA system itself.

A set of answer sequences can be seen in rows 130-134. The set of answer sequences are an ordered sequence of treatment answers (or answers), ordered based on a category sequence. Thus, in FIG. 1 a first answer sequence can be seen in row 130 that includes treatment answer 110 related to chemotherapy A, then treatment answer 112 related to surgery A, then treatment answer 114 related to endocrine therapy A, then treatment answer 116 related to radiation treatment A. The first answer sequence suggests a treatment plan of the various treatment answers 110-116 performed in order according to the category sequence 109. In embodiments an answer sequence can be referred to as a treatment plan. In embodiments a treatment plan is an answer sequence generated from treatment answers ordered according to a treatment template, as described herein.

In some embodiments, answer sequences can include answers from a portion of answer categories in a category sequence. For example, in row 132 and 134, second and third answer sequences can be seen respectively. The second answer sequence includes treatment answers 118, 120, 122 from answer categories 102, 104, and 108. The second answer sequence does not include a treatment answer from answer category 106.

Referring now to FIG. 2 a block diagram of an example computing environment 200 for use with a QA system can be seen, according to embodiments of the present disclosure. In some embodiments, the computing environment 200 can include one or more remote devices 202, 212 and one or more host devices 222. Remote devices 202, 212 and host device 222 can be distant from each other and communicate over a network 250. In embodiments, the host device 222 can be a central hub from which remote devices 202, 212 establish a communication connection. In embodiments, the host device and remote devices can be configured in various suitable relationships (e.g., in a peer-to-peer or other relationship).

In some embodiments, the network 250 can be implemented by suitable communications media (e.g., wide area network (WAN), local area network (LAN), Internet, and Intranet). In some embodiments, remote devices 202, 212 and host devices 222 can be local to each other, and communicate via appropriate local communication medium (e.g., local area network (LAN), hardwire, wireless link, Intranet). In some embodiments, the network 250 can be implemented within a cloud computing environment, or using one or more cloud computing services. Consistent with various embodiments, a cloud computing environment can include a network-based, distributed data processing system that provides one or more cloud computing services. Further, a cloud computing environment can include multiple computers (e.g., hundreds or thousands of them or more), disposed within one or more data centers and configured to share resources over the network 250.

In some embodiments, host device 222 can include a QA system 230 having a search application 234 and an answer module 232. The search application 234 can be configured to search one or more databases or other computer systems for content that is related to an input query by a user at a remote device 202, 212.

In some embodiments, remote devices 202, 212 can enable users to submit input queries (e.g., search requests or other user queries) to host device 222 to retrieve search results. For example, the remote devices 202, 212 can include a query module 210, 220 (e.g., in the form of a web browser or other suitable software module) and present a graphical user interface or other interface (command line prompts, menu screens, etc.) to solicit queries from users for submission to one or more host devices 222 and to display answers/results obtained from the host devices 222 in relation to such user queries (e.g., answer sequences).

Consistent with various embodiments, host device 222 and remote devices 202, 212 can be computer systems, and can each be equipped with a display or monitor. The computer systems can include at least one processor 206, 216, 226; memories 208, 218, 228; internal or external network interface or communications devices 204, 214, 224 (e.g., modem, network interface cards); optional input devices (e.g., a keyboard, mouse, touchscreen, or other input device); and commercially available or custom software (e.g., browser software, communications software, server software, natural language processing software, search engine and/or web crawling software, filter modules for filtering content based upon predefined criteria). In some embodiments, the computer systems can include servers, desktops, laptops, and hand-held devices. In addition, the answer module 232 can include one or more modules or units to perform the various functions of embodiments as described below, and can be implemented by a combination of software and/or hardware modules or units.

Figure 3:
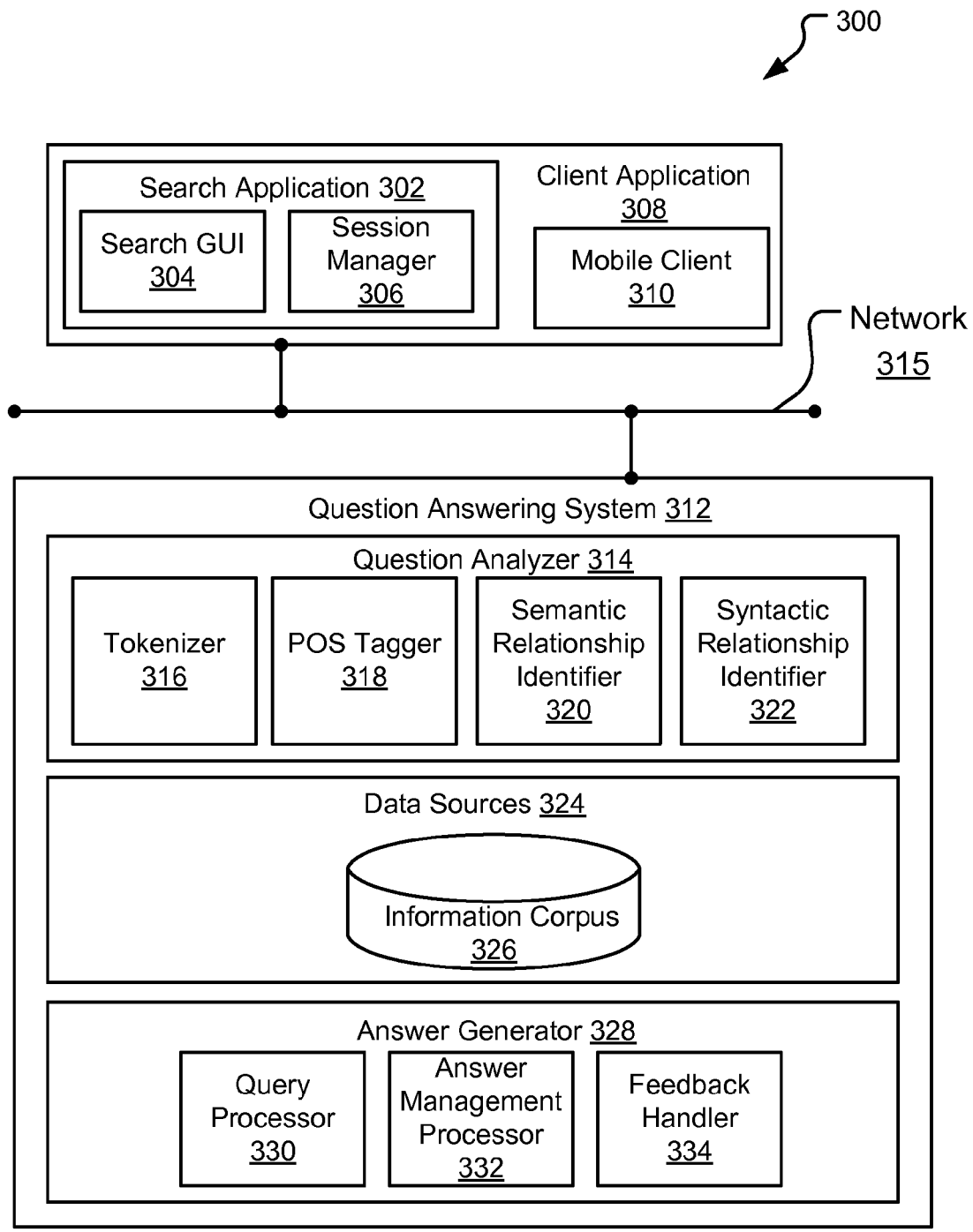
FIG. 3 depicts a block diagram of an example QA system configured to generate answers in response to one or more input queries, according to embodiments of the present disclosure.

Referring now to FIG. 3 a block diagram of a QA system can be seen, according to embodiments of the present disclosure. Aspects of FIG. 3 are directed toward a system architecture 300, including a QA system 312 to generate a group of answers (or groups of answer sequences) in response to an input query. In some embodiments, one or more users can send requests for information to QA system 312 using a remote device (such as remote devices 202, 212 of FIG. 2). The remote device can include a client application 308 which can include one or more entities operable to generate information that is dispatched to QA system 312 via network 315. QA system 312 can be configured to perform methods and techniques for responding to the requests sent by the client application 308. In some embodiments, the information received at QA system 312 can correspond to input queries received from users, where the input queries can be expressed in natural language, or images, or other forms.

An input query (similarly referred to herein as a question) can be one or more words that form a search term or request for data, information, or knowledge. A question can be expressed in the form of one or more keywords. Questions can include various selection criteria and search terms. A question can be composed of complex linguistic features in addition to keywords. However, a keyword-based search for answers can also be possible. In some embodiments, using restricted syntax for questions posed by users can be enabled. The use of restricted syntax can result in a variety of alternative expressions that assist users in better stating their needs. In some embodiments, questions can be implied (rather than explicit) questions. Furthermore, in some embodiments, questions can be audio-type (e.g., spoken-word recordings, music, scientific sound recordings), video-type (e.g., a film, a silent movie, a video of a person asking a detailed question), image-type (e.g., a picture, a photograph, a drawing), or other type that can be received and processed by the QA system.

In some embodiments, client application 308 can operate on a variety of devices. Such devices can include, but are not limited to, mobile and hand-held devices (e.g., laptops, mobile phones, personal or enterprise digital assistants, and the like), personal computers, servers, or other computer systems that can access the services and functionality provided by QA system 312. In some embodiments, client application 308 can include one or more components, such as a mobile client 310. Mobile client 310, acting as an agent of client application 308, can dispatch user query requests to QA system 312.

Consistent with various embodiments, client application 308 can also include a search application 302, either as part of mobile client 310 or separately, that can perform several functions, including some or all of the above functions of mobile client 310 listed above. For example, in some embodiments, search application 302 can dispatch requests for information to QA system 312. In some embodiments, search application 302 can be a client application to QA system 312. Search application 302 can send requests for answers to QA system 312. Search application 302 can be installed on a personal computer, a server, or other computer system.

In some embodiments, search application 302 can include a search graphical user interface (GUI) 304 and session manager 306. In such situations, users can be able to enter questions in search GUI 304. In some embodiments, search GUI 304 can be a search box or other GUI component, the content of which can represent a question to be submitted to QA system 312. Users can authenticate to QA system 312 via session manager 306. In some embodiments, session manager 306 can keep track of user activity across sessions of interaction with the QA system 312. Session manager 306 can also keep track of what questions are submitted within the lifecycle of a session of a user. For example, session manager 306 can retain a succession of questions posed by a user during a session. In some embodiments, answers produced by QA system 312 in response to questions posed throughout the course of a user session can also be retained. Information for sessions managed by session manager 306 can be shared between various computer systems and devices.

In some embodiments, client application 308 and QA system 312 can be communicatively coupled through network 315, e.g., the Internet, intranet, or other public or private computer network. In some embodiments, QA system 312 and client application 308 can communicate by using Hypertext Transfer Protocol (HTTP) or Representational State Transfer (REST) calls. In some embodiments, QA system 312 can reside on a server node. Client application 308 can establish server-client communication with QA system 312 or vice versa. In some embodiments, the network 315 can be implemented within a cloud computing environment, or using one or more cloud computing services.

Consistent with various embodiments, QA system 312 can respond to a request for information sent by client applications 308 (e.g., question posed by a user). QA system 312 can generate a group of answers in response to the request. In some embodiments, QA system 312 can include a question analyzer 314, data sources 324, and answer generator 328. Question analyzer 314 can be a computer module that analyzes the received questions. Question analyzer 314 can perform various methods and techniques for analyzing the questions (syntactic analysis, semantic analysis, image recognition analysis, etc.). In some embodiments, question analyzer 314 can parse received questions. Question analyzer 314 can include various modules to perform analyses of received questions. For example, computer modules that question analyzer 314 can encompass include, but are not limited to, a tokenizer 316, part-of-speech (POS) tagger 318, semantic relationship identifier 320, and syntactic relationship identifier 322.

In some embodiments, tokenizer 316 can be a computer module that performs lexical analysis. Tokenizer 316 can convert a sequence of characters into a sequence of tokens. A token can be a string of characters typed by a user and categorized as a meaningful symbol. Further, in some embodiments, tokenizer 316 can identify word boundaries in an input query and break the question or text into its component parts such as words, multiword tokens, numbers, and punctuation marks. In some embodiments, tokenizer 316 can receive a string of characters, identify the lexemes in the string, and categorize them into tokens.

Consistent with various embodiments, POS tagger 318 can be a computer module that marks up a word in a text to correspond to a particular part of speech. POS tagger 318 can read a question or other text in natural language and assign a part of speech to each word or other token. POS tagger 318 can determine the part of speech to which a word corresponds based on the definition of the word and the context of the word. The context of a word can be based on its relationship with adjacent and related words in a phrase, sentence, question, or paragraph. In some embodiments, the context of a word can be dependent on one or more previously posed questions. Examples of parts of speech that can be assigned to words include, but are not limited to, nouns, verbs, adjectives, adverbs, and the like. Examples of other part of speech categories that POS tagger 318 can assign include, but are not limited to, comparative or superlative adverbs, wh-adverbs, conjunctions, determiners, negative particles, possessive markers, prepositions, wh-pronouns, and the like. In some embodiments, POS tagger 318 can tag or otherwise annotate tokens of a question with part of speech categories. In some embodiments, POS tagger 318 can tag tokens or words of a question to be parsed by QA system 312.

In some embodiments, semantic relationship identifier 320 can be a computer module that can identify semantic relationships of recognized entities (e.g., words, phrases) in questions posed by users. In some embodiments, semantic relationship identifier 320 can determine functional dependencies between entities and other semantic relationships.

Consistent with various embodiments, syntactic relationship identifier 322 can be a computer module that can identify syntactic relationships in a question composed of tokens posed by users to QA system 312. Syntactic relationship identifier 322 can determine the grammatical structure of sentences, for example, which groups of words are associated as "phrases" and which word is the subject or object of a verb. Syntactic relationship identifier 322 can conform to formal grammar.

In some embodiments, question analyzer 314 can be a computer module that can parse a received user query and generate a corresponding data structure of the user query. For example, in response to receiving a question at QA system 312, question analyzer 314 can output the parsed question as a data structure. In some embodiments, the parsed question can be represented in the form of a parse tree or other graph structure. To generate the parsed question, question analyzer 314 can trigger computer modules 316-322. Additionally, in some embodiments, question analyzer 314 can use external computer systems for dedicated tasks that are part of the question parsing process.

In some embodiments, the output of question analyzer 314 can be used by QA system 312 to perform a search of a set of (i.e., one or more) corpora to retrieve information to answer a question posed by a user. As used herein, a corpus can refer to one or more data sources. In some embodiments, data sources 324 can include databases, information corpora, data models, and document repositories. In some embodiments, the data source 324 can include an information corpus 326. The information corpus 326 can enable data storage and retrieval. In some embodiments, the information corpus 326 can be a storage mechanism that houses a standardized, consistent, clean and integrated form of data. The data can be sourced from various operational systems. Data stored in the information corpus 326 can be structured in a way to specifically address reporting and analytic requirements. In some embodiments, the information corpus can be a relational database. In some example embodiments, data sources 324 can include one or more document repositories.

In some embodiments, answer generator 328 can be a computer module that generates the group of answers in response to posed questions. Examples of answers generated by answer generator 328 can include, but are not limited to, natural language sentences, reports, charts, or other analytic representation, raw data, web pages, and the like. In some embodiments, answers can be of audio type, image type, or other suitable medium type.

In some embodiments, answer generator 328 can include query processor 330, answer management processor 332, and feedback handler 334. When information in the data source 324 matching a parsed question is located, a technical query associated with the pattern can be executed by query processor 330. Based on data retrieved by a technical query executed by query processor 330, answer management processor 332 can be configured to organize the retrieved answers. In embodiments, the answer management processor 332 can be a visualization processor configured to render a visualization of the organized answers. In embodiments, the rendered visualization of the answers can represent the answer to the input query. In some embodiments, answer management processor 332 can organize the answers according to various forms including, but not limited to, images, charts, tables, dashboards, maps, and the like.

Described further herein, the answer management processor 332 can be configured to implement embodiments of the present disclosure. For example, the answer management processor 332 can be configured to sort, based on a set of answer categories, a first set of answers into a first answer category and a second set of answers into a second answer category. The answer categories can be the same or substantially similar as described herein.

The answer management processor 332 can be configured to determine, using the subject matter, a category sequence including the first answer category and the second answer category. The answer management processor 332 can be configured to establish, based on the category sequence, a first answer sequence established from a portion of the first set of answers from the first answer category and a portion of the second set of answers from the second answer category.

In some embodiments, feedback handler 334 can be a computer module that processes feedback from users on answers generated by answer generator 328. In some embodiments, users can be engaged in dialog with the QA system 312 to evaluate the relevance of received answers. For example, the answer generator 328 could produce the group of answers corresponding to a question submitted by a user. The user could rank each answer according to its relevance to the question. In some embodiments, the feedback of users on generated answers can be used for future question answering sessions.

The various components of the exemplary QA system described above can be used to implement various aspects of the present disclosure. For example, the client application 308 could be used to receive an input query from a user. The question analyzer 314 could, in some embodiments, be used to analyze input queries and to generate the group of answers based on the input query. The answer generator 328 could, in some embodiments, be used to render visualization of the group of answers to generate an answer sequence for presentation to the user.

Figure 4:
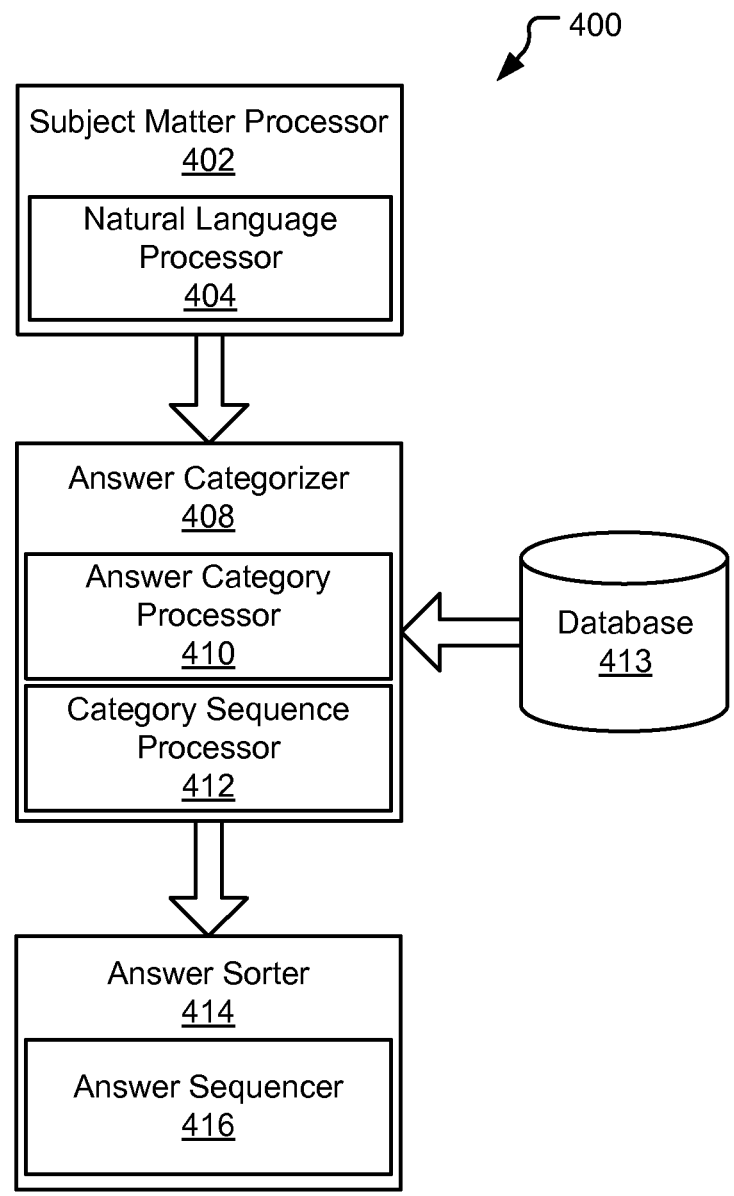
FIG. 4 depicts a system architecture configured to manage answers generated by an example QA system, according to embodiments of the present disclosure.

Referring now to FIG. 4, a block diagram of a system architecture 400 for answer management in a question-answering (QA) environment can be seen, according to embodiments of the present disclosure. In embodiments, the system architecture 400 can represent an example architecture for executing embodiments of the present disclosure. For example, in some instances, the system architecture 400 could be an example representation of the answer management processor 332 (FIG. 3).

In embodiments, the system architecture 400 can include a subject matter processor 402, an answer categorizer 408, and an answer sorter 414.

The subject matter processor 402 can be a computer module configured to determine a subject matter for data in the QA environment. As described herein, data in the QA environment can include one or more input queries and/or the group of answers generated in response to the input queries. In embodiments, the subject matter can be contextual information for the data in the QA environment. The subject matter can be used to organize the group of answers, as described herein. For example, described further herein, the subject matter can be used to determine one or more answer categories for the group of answers. In some examples, the subject matter can be used to determine one or more category sequences. For example, if the subject matter is oncology then the sequences may include chemotherapy treatments and radiation treatments, but an alternative category of computer troubleshooting might be left out because it is irrelevant to oncology.

In embodiments, the subject matter processor 402 can determine the subject matter by receiving a subject matter selection from a user. For example, the user could select computer troubleshooting as the subject matter of data in the QA environment. A system could then act accordingly in determining answer categories and/or category sequences, described further herein.

In some embodiments, the subject matter processor 402 can be configured to determine the subject matter based on natural language analysis of data in the QA environment.

In embodiments, the subject matter processor 402 can include a natural language processor 404. The natural language processor 404 can be configured to perform various methods and techniques for natural language analysis of data in the QA environment. For example, the natural language processor 404 can be configured to perform syntactic analysis, semantic analysis, image recognition analysis, concept matching and other suitable methods and techniques.

In embodiments, the subject matter can be determined by concept matching techniques. Concept matching techniques can include, but is not limited to, semantic similarity, syntactic analysis, and ontological matching. For example, in embodiments, the natural language processor could be configured to parse data in the QA environment to determine semantic features (e.g. repeated words, keywords, etc.) and/or syntactic features (e.g. location of semantic features in headings, title, etc.) in the data. Ontological matching could be used to map semantic and/or syntactic features to a particular concept. The concept can then be used to determine the subject matter for the data.

For example, in some embodiments, the natural language processor 404 can be configured to parse the group of answers generated in response to the input query. Natural language processor 404 could identify, in the group of answers, repeated words corresponding to a particular type of cancer. Additionally, the natural language processor 404 could identify the location of the repeated words in headings and titles, which can indicate the relative importance of the repeated words. Based on the semantic and syntactic features the natural language processor 404 could map the group of answers to a particular concept, such as oncology. In embodiments, the subject matter processor 402 could be configured to select the concept as the subject matter.

The answer categorizer 408 can be configured to determine a set of answer categories for the group of answers. As described herein, the answer categories are classifications that can be applied to the group of answers to assist in organization of the answers. For example, the group of answers generated in response to a question about how to troubleshoot a computer could include answers related to troubleshooting hardware and troubleshooting software. A first set of answers corresponding to hardware troubleshooting could be sorted into a first answer category corresponding to hardware troubleshooting. A second set of answers corresponding to software troubleshooting could be sorted into a second answer category corresponding to software troubleshooting.

Additionally, the answer categorizer 408 can be configured to determine a category sequence for the answer categories. The answer categorizer can include an answer category processor 410 and a category sequence processor 412.

The answer category processor 410 can be configured to determine one or more answer categories for the group of answers. In embodiments, the answer categories can be determined based on the subject matter of data in the QA environment. For example, a subject matter related to oncology could have different answer categories than a subject matter related to computer troubleshooting. In some embodiments, answer categories can be shared between subject matter. In embodiments, the answer category processor 410 can use the subject matter determination from the subject matter processor 402 to determine the one or more answer categories.

In embodiments, the answer category processor 410 can determine one or more answer categories by accessing a repository of predefined answer categories. In embodiments, the repository of predefined answer categories can be stored in a database 413. In embodiments, the database 413 can include one or more answer categories that correspond to various subject matter. For example, a set of answer categories including radiation, chemotherapy, endocrine therapy, and surgery could correspond to the subject matter of oncology. Thus, when the subject matter is oncology, the answer category processor 410 could access the set of answer categories corresponding to oncology. Additionally, a set of answer categories including hardware troubleshooting and software troubleshooting could correspond to the subject matter of IT support. In embodiments, various suitable answer categories can also be selected for various subject matter.

In some embodiments, the answer category processor 410 can determine the answer categories based on natural language analysis of data in the QA environment. For example, in embodiments, the answer category processor 410 could be configured to analyze the input query, using a natural language processing technique. Based on the analysis, the answer category processor 410 could determine the answer categories.

In some embodiments, the answer category processor 410 could be configured to analyze the group of answers, using a natural language processing technique. Based on the analysis, the answer category processor 410 could determine the answer categories.

The category sequence processor 412 can be configured to determine one or more category sequences. In embodiments, the category sequence processor 412 can be configured to determine the one or more category sequences based on the subject matter. In embodiments, the category sequence processor 412 can determine one or more category sequences by accessing a repository of predefined category sequences. In embodiments, the repository of predefined category sequences can be stored in a database 413. In embodiments, the database 413 can include one or more category sequences that correspond to various subject matters. For example, a category sequence of first surgery, then radiation, then chemotherapy, and then endocrine therapy could correspond to the subject matter of oncology. In embodiments, various category sequences can be selected for various subject matters. In some embodiments, a category sequence processor may be able to weed out/not include category sequences that are not relevant or are impractical.

The answer sorter 414 can be configured to sort the group of answers into the various answer categories. The answer sorter 414 can sort the group of answers by classifying answers as related to one or more of the answer categories. For example, the answer sorter 414 could sort a first set of answers into a first answer category by classifying the first set of answers as related to the first answer category.

In embodiments, the answer sorter 414 can use natural language analysis to sort the group of answers. For example, in embodiments, the answer sorter 414 can parse the group of answers to identify semantic features which correspond to one or more of the answer categories. The answer sorter 414 could then sort answers of the group of answers into answer categories that correspond to the identified semantic features.

In some embodiments, the answer sorter can sort the group of answers using concept matching techniques, as described herein.

The answer sorter can include an answer sequencer 416. The answer sequencer 416 can be configured to generate one or more answer sequences. In embodiments, the answer sequencer 416 can generate the one or more answer sequences based on the group of answers and the one or more category sequences. For example, the answer sequencer can assemble an answer sequence including the group of answers from each answer category included within a given category sequence, the group of answers ordered based on a category sequence.

In an additional example, the answer sorter 414 could sort a first set of answers into a first answer category and a second set of answers into a second answer category. From the category sequence processor 412, a category sequence could include the first answer category followed by the second answer category. The answer sequencer 416 could generate one or more answer sequences from the first and second sets of answers. For example, an answer sequence could include a first answer from the first set of answers followed by a second answer from the second set of answers. In embodiments, the answer sequencer could generate various possible combinations of answers in the first and second set of answers to generate the one or more answer sequences. In embodiments, the one or more answer sequences can then be presented as an answer to an input query.

Figure 5:
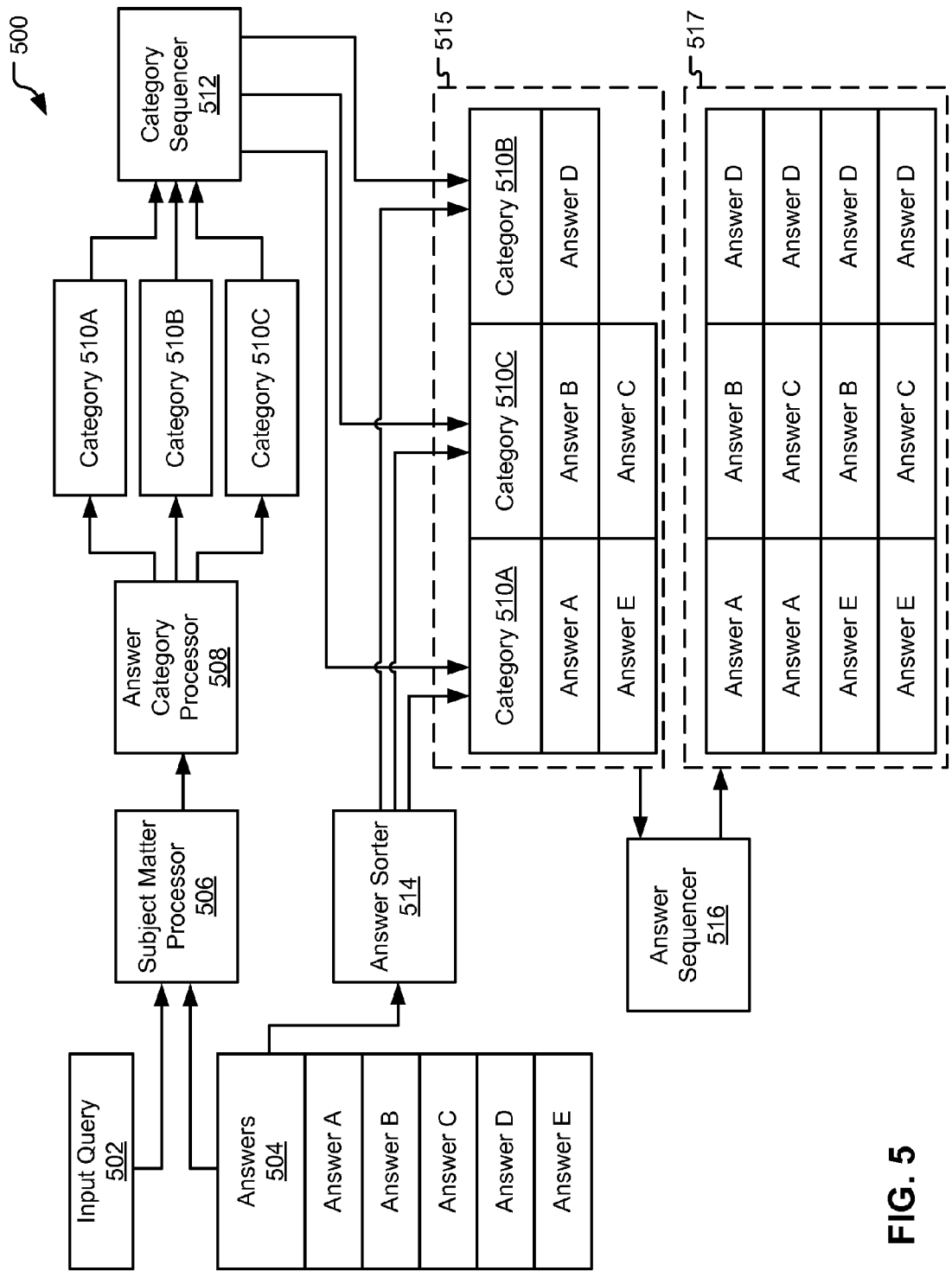
FIG. 5 depicts a diagram of using answer management to generate one or more answer sequences, according to embodiments of the present disclosure.

Referring now to FIG. 5, a diagram 500 of answer management can be seen according to embodiments of the present disclosure. The diagram depicts a system including a subject matter processor 506, an answer category processor 508, a category sequencer 512, an answer sorter 514, and an answer sequencer 516.

Data in the QA environment, such as an input query 502 and the group of answers 504 generated in response to the input query 502, can be inputted to the subject matter processor 506. The subject matter processor 506 can be the same or substantially similar to the subject matter processor 402 (FIG. 4) as described herein. The subject matter processor 506 can be configured to determine a subject matter for data in the QA environment, and the subject matter can be used, as described herein, to determine answer categories and category sequences for the QA system.

The answer category processor 508 can be configured to determine answer categories for the QA system. The answer category processor 508 can be the same or substantially similar to answer category processor 410 (FIG. 4). The answer category processor can determine a set of answer categories 510A-510C by accessing a database of answer categories corresponding to the subject matter.

Category sequencer 512 can be configured to determine a category sequence of the answer categories 510A-510C. For example, category sequencer 512 could determine a category sequence of the first answer category 510A, then the third answer category 510C, and then the second answer category 510B. In embodiments, the category sequencer 512 can determine the category sequence by accessing a database of category sequences corresponding to the subject matter.

Answer sorter 514 can be configured to sort the group of answers 504 into the answer categories 510A-510C. Answer sorter 514 can be the same or substantially similar as the answer sorter 414 (FIG. 4). As seen in FIG. 5, answer sorter 514 can be configured to sort the group of answers 504 into the set of answer categories 510A-510C to form a set of sorted answers 515. For example, answer A and answer E are sorted into answer category 510A. Answer B and answer C are sorted into answer category 510C, and answer D is sorted into category 510B.

The answer sequencer 516 can be configured to generate one or more answer sequences 517 from the set of sorted answers 515. The answer sequencer 517 can be the same or substantially similar as the answer sequencer 416 (FIG. 4). The answer sequencer can be configured to generate one or more answer sequences 517 by selecting an answer from one or more answer categories in order according to the category sequence. For example, the one or more answer sequences 517 could include an answer sequence of answer A, then answer B, and then answer D. As seen in FIG. 5, answer sequencer 516 can form the one or more answer sequences 517 from various combinations of the sorted answers 515 in order according to the category sequence. The one or more answer sequences can be presented to a user to satisfy the input query 502.

Figure 6:
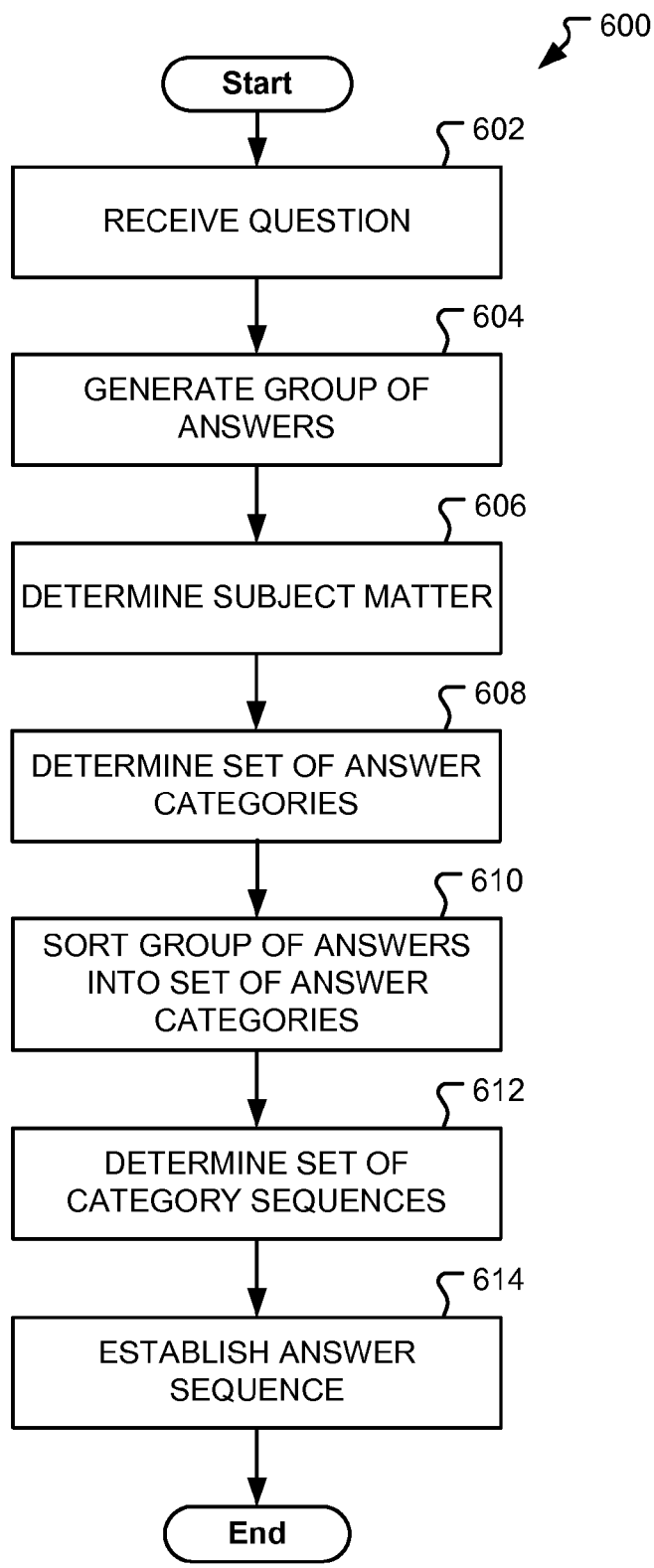
FIG. 6 depicts a flowchart diagram of a method of answer management in a QA environment, according to embodiments of the present disclosure.

Referring now to FIG. 6, a flowchart diagram of a method 600 of answer management in a question-answering (QA) environment can be seen according to embodiments of the present disclosure. In operation 602, an input query can be received. The input query can be a request for data to a QA system from a user. The input query can be the same or substantially similar as described herein. In operation 604, a group of answers can be generated. The group of answers can be generated by an answer generator in the QA system by retrieving answers from data sources, such as databases and/or information corpora.

In operation 606, a subject matter can be determined. The subject matter can be the same or substantially similar as described herein. The subject matter can be contextual information related to data in the QA environment. For example, in embodiments, the subject matter could be the topic of the input query. In some examples, the subject matter could be the topic of the group of answers generated in response to the input query.

In operation 608, a set of answer categories can be determined. The set of answer categories can be the same or substantially similar as described herein. The answer categories can be classifications for the group of answers to assist in organization of the answers. In embodiments, an answer category can be a high level description of an action suggested by an answer, as described herein.

In operation 610, the group of answers can be sorted into the set of answer categories. The group of answers can be sorted by classifying answers as related to one or more of the answer categories. For example, a first set of answers could be sorted into a first answer category by classifying the first set of answers as related to the first answer category. In embodiments, the answers can be sorted into the answer categories using natural language analysis as described herein.

In operation 612, a set of category sequences can be determined. The category sequences can be the same or substantially similar as described herein. Described herein, the category sequence can be various sequences of answer categories. As described herein, the category sequences can be determined based on the subject matter. In embodiments, the set of category sequences can be accessed from a database by a QA system. For example, one or more category sequences could be predetermined and stored for access when the QA system is tasked with a subject matter corresponding to the set of category sequences.

In operation 614, an answer sequence can be established. The answer sequence can be the same or substantially similar as described herein. As described herein, the answer sequence can be formed by selecting the group of answers from one or more answer categories in order according to the category sequence.

Figure 7:
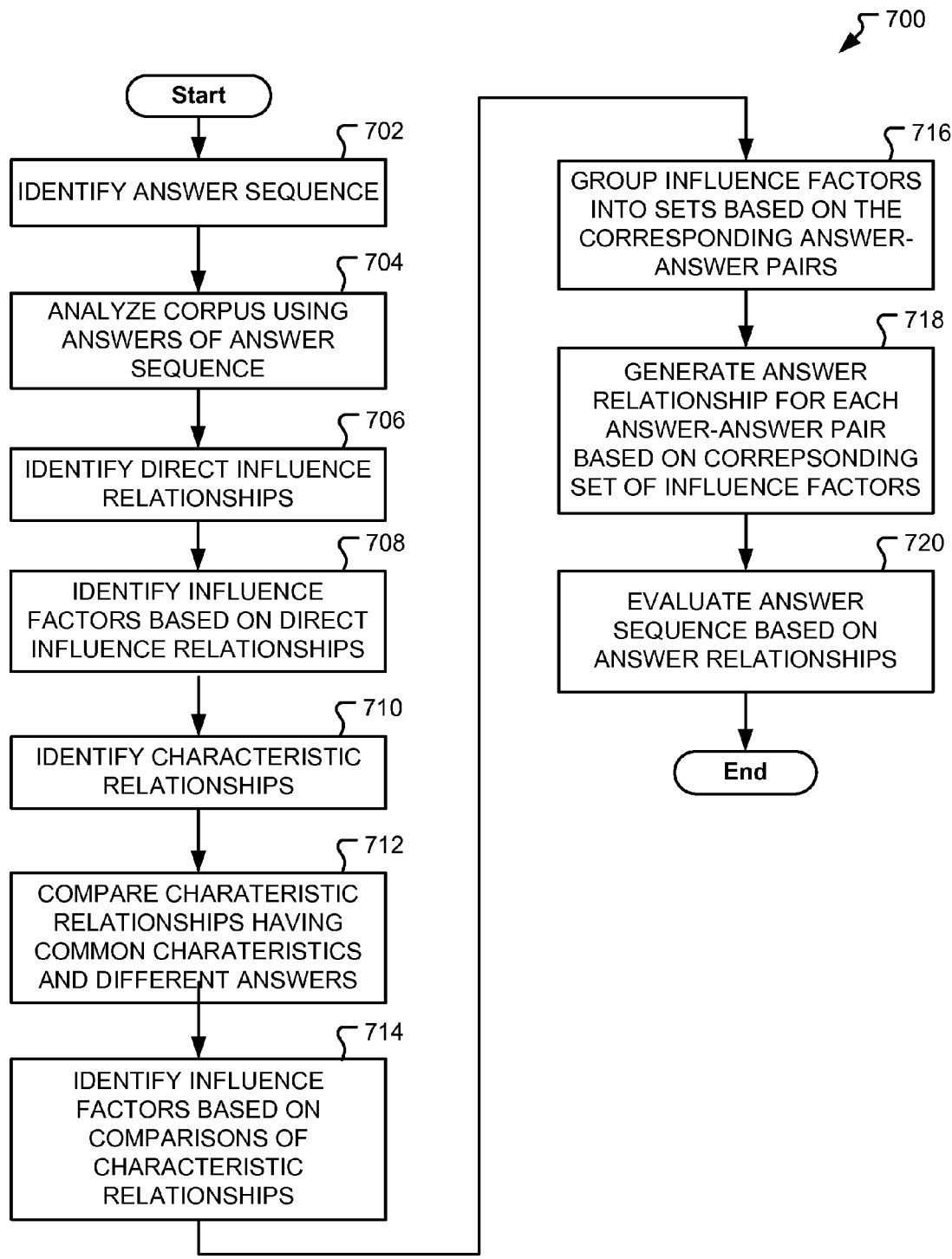
FIG. 7 depicts a flowchart diagram of a method of answer relationship management in a QA environment, according to embodiments of the present disclosure.

Referring now to FIG. 7, a flowchart diagram of a method 700 of answer relationship management in a QA environment can be seen according to embodiments of the present disclosure. In operation 702, an answer sequence can be identified. The answer sequence can include any number of answers. In some embodiments, the answer sequence can be generated using some or all of the operations of method 600 as shown in FIG. 6. In operation 704, a corpus can be analyzed using the answers of the answer sequence. In some embodiments, this can take the form of a keyword search with the answers acting as keywords. Further, in some embodiments, the analysis can include parsing the corpus based on the answers.

In operations 706-714, influence factors can be identified through direct influence relationship evaluations (per operations 706 and 708) and/or through characteristic relationship evaluations (per operations 710, 712, and 714). In some embodiments, influence factors may be identified based on sentiment factors (which are described elsewhere herein) associated with two or more answers. Further, in some embodiments, influence factors may be the same or substantially similar to influence components (which are also described elsewhere herein). As described herein, an influence factor can be an interaction or result that is likely to occur if two answers of an answer-answer pair of an answer sequence are both used as provided for in that particular answer sequence. Further, an influence factor can be a description or an evaluation (in terms of positive or negative, likely or unlikely, etc.) of an effect that one answer is known to have on another answer (one direction influence) or that two answers are known to have on each other (two direction influence). Further, an influence factor can be a measure of or information about the compatibility of two answers of an answer sequence that is inferred based on the interactions between each of the two answers and one or more common (e.g., shared) concepts. As an example in the field of baking, consider a scenario wherein an answer sequence includes a first answer of "add ingredient A" and a second answer of "stir immediately". In this scenario several different influence factors are possible. For example, if ingredient A gets badly clumpy if it is stirred immediately, then influence factors of "likely to causing clumping of ingredient A" or "second answer likely to cause negative influence on first answer" are possible.

In operation 706, direct influence relationships within answer-answer pairs can be identified based on the analysis of the corpus. As described herein, a direct influence relationship can be an explicit, immediate relationship between the answers of the particular answer-answer pair. Further, a direct influence relationship can also be a first-degree connection between the answers of the answer-answer pair as discovered based on the analysis of the corpus. For example, in the field of oncology, in an answer sequence including a first answer of "treat patient with chemotherapy A for four weeks" and a second answer of "treat patient with endocrine therapy Y", there could be a direct influence relationship between the first and second answers that could be discovered in a corpus (e.g., a medical journal) that includes a passage stating that "[a] patient should not be treated with endocrine therapy Y if the patient has received or will receive more than one week of chemotherapy A." In operation 708, influence factors can be identified based on the direct influence relationships identified in operation 706. In this oncology example, a strongly negative influence factor could be identified as corresponding to the first answer and the second answer based on the medical journal passage.

In operation 710, characteristic relationships between answers and characteristics can be identified based on the analysis of the corpus. As described herein, a characteristic can refer to an element, feature, or trait. Further as described herein, a characteristic relationship can refer to a relationship between a particular answer of an answer sequence and a particular characteristic. In some embodiments, a characteristic relationship can include or be labeled with attributes that describe, are evidence of, and/or quantify the nature of the relationship between the answer and the characteristic. For example, in the field of IT support, an answer of "install new CPU" could have characteristic relationships with characteristics of "expensive" and "easy to perform" (e.g., where there is a first relationship between a step of installing a new CPU and a characteristic of being expensive and where there is a second relationship between the step of installing a new CPU and the characteristic of being easy to perform). In this example, the characteristic relationship between "install new CPU" and "expensive" could include the attribute of "approximately $700" (e.g., where having a cost of approximately $700 is evidence of why installing a new CPU has a relationship with the characteristic of expensive) and the characteristic relationship between "install new CPU" and "easy to perform" could include a negative correlation (e.g., where installing a new CPU is considered not easy to perform).

In operation 712, comparisons can be made between characteristic relationships having common (e.g. shared) characteristics and different (e.g., non-shared) answers within an answer sequence. In operation 714, based on the comparisons of these characteristic relationships, influence factors can be identified as corresponding to the answers of these characteristic relationships. The comparison of characteristic relationships is described in reference to FIG. 8.

In operation 716, influence factors identified in operations 706-714 can be grouped into sets of influence factors based on the answer-answer pair to which each influence factor belongs. For example, in an answer sequence including answers E, F, G, and H, there can be, in some embodiments, up to six different answer pairs (E-F, E-G, E-H, F-G, F-H, and G-H) and, therefore, up to six different sets of influence factors into which a given influence factor could be grouped. In operation 718, answer relationships are generated for each possible answer-answer pair based on the set of influence factors corresponding to both answers of that answer-answer pair. Each answer relationship can represent a composite of a particular set of influence factors. In some embodiments, answer relationships can be measures or indicators as to how answers are likely to interact or influence each other (or influence the answer sequence as a whole) if the answer sequence is used. Further, in some embodiments, for answer-answer pairs having no shared influence factors, there can be deemed to be no answer relationship between those answers forming the pair or there can be deemed to be a null or neutral answer relationship. For instance, to continue the EFGH example above, if there are no influence factors corresponding to the E-F pair then the relationship between answer E and answer F may be deemed a neutral answer relationship. In operation 720, the identified answer sequence can be evaluated based on the answer relationships.

To aid understanding, a simplified version of method 700 is performed in an example scenario. In this example, a question of "What steps should I take to get a beautiful lawn on my property in Arizona?" is provided by a homeowner to a QA system. The QA system identifies several answer sequences (per operation 702). One of the answer sequences includes a first answer of "plant grass variety X in the spring" and a second answer of "add fertilizer Y to the lawn in the summer". In this example, both answers are included in the answer sequence at least in part because the QA system determines that they both work well in hot, dry climates. A corpus of lawn and gardening magazines is analyzed by the QA system using the two answers (per operation 704). In the analysis, a passage is discovered that states that "[f]ertilizer Y has been shown to work poorly on some lawns having grass variety X." Based on this passage, a direct influence relationship between the answers is identified (per operation 706). Based on the direct influence relationship a negative influence factor corresponding to both answers is identified (per operation 708). Also based on the analysis of the corpus, characteristic relationships are identified between each answer and a characteristic of "tolerates hot climates" (per operation 710). Because these characteristic relationships have this shared characteristic, they are compared (per operation 712). Based on the comparison, a positive characteristic-based influence factor is identified as corresponding to both answers (per operation 714). The direct influence factor and the characteristic-based influence factor are grouped together to form the set of influence factors corresponding to both answers (per operation 716). Based on the set of influence factors (in this instance, the two influence factors), an answer relationship is generated between the two answers (per operation 718). In this example, the negative direct influence factor and the positive characteristic-based influence factor are weighed against each other, but overall the negative influence factor is weighted more heavily (e.g., where the negative influence factor is determined to be more influential) and the resulting answer relationship is negative. Based on the answer relationship, the answer sequence is evaluated (per operation 720). In this instance, because of the negative answer relationship, the confidence score of the answer sequence is decreased and, as a result, this particular answer sequence is presented to the homeowner with a lower ranking (relative to the other answer sequences) than would have been the case had the answer relationship not been considered.

Figure 8:
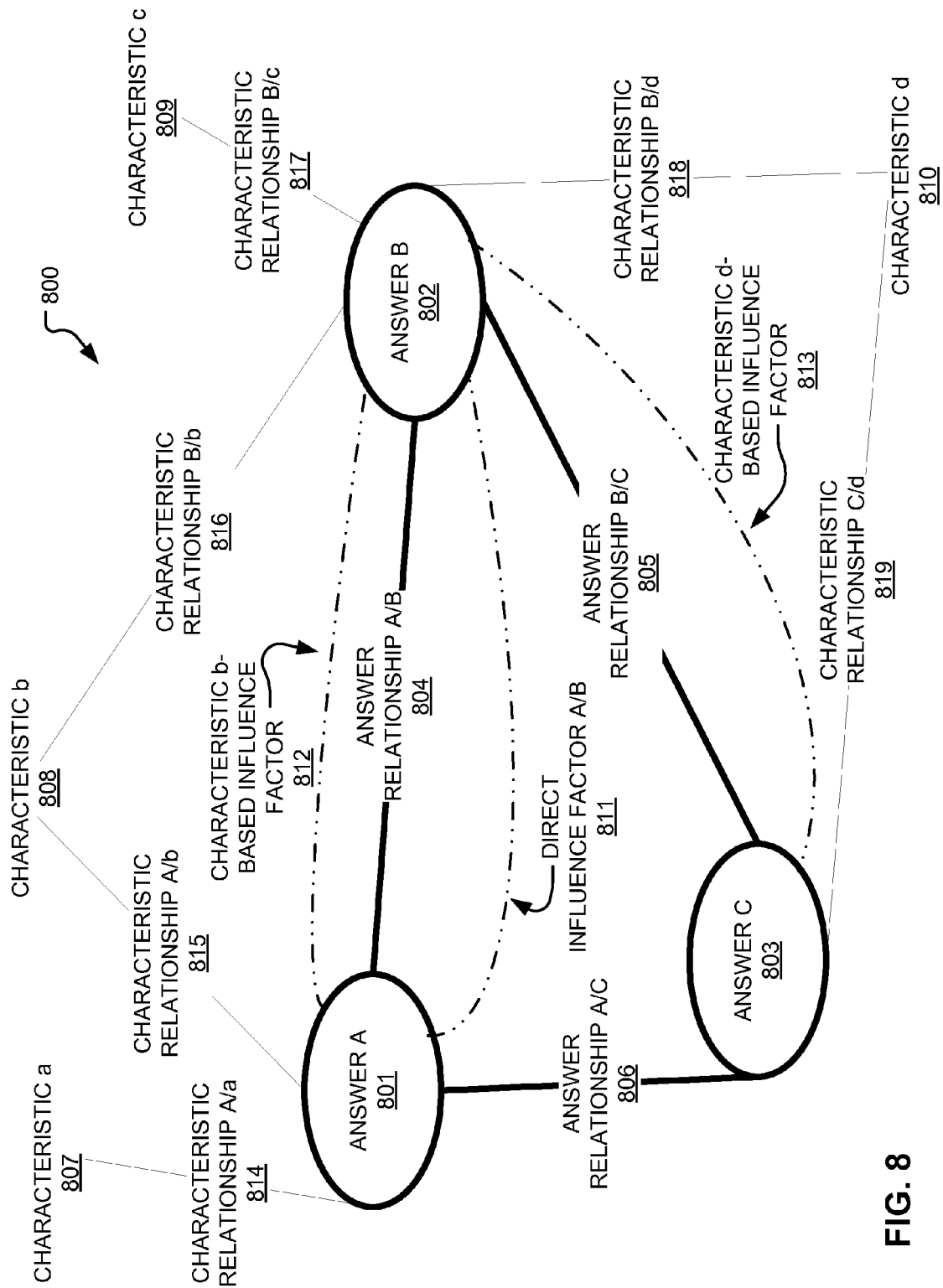
FIG. 8 depicts a diagram of an example labeled answer sequence including characteristic relationships, direct influence relationships, and answer relationships, according to embodiments of the present disclosure.

Referring now to FIG. 8, a diagram of an example labeled answer sequence 800 including characteristic relationships, direct influence relationships, and answer relationships can be seen, according to embodiments of the present disclosure. As shown, example answer sequence 800 includes answer A 801, answer B 802, and answer C 803. In some embodiments, this means that answer sequence 800 could include a multitude of different orderings or combinations of these three answers (answer A followed by answer B followed by answer C, answer A and answer C occurring at substantially the same time followed by answer B, etc.). In some embodiments, the exact ordering of the answers may or may not matter for the purpose of establishing answer relationships (for example, in some embodiments, answer sequence ABC could be treated the same as answer sequence BCA).

As shown, there is only one direct influence factor of interest in evaluating answer sequence 800. Specifically, there is a direct influence factor A/B 811 corresponding to both answer A 801 and answer B 802. This direct influence factor A/B 811 can be based on a direct influence relationship between answer A 801 and answer B 802. Also shown are four characteristics (a, b, c, and d) 807-810 and six characteristic relationships (A/a, A/b, B/b, B/c, B/d, and C/d) 814-819. Two pairs of characteristic relationships (A/b and B/b, B/d and C/d), 815 and 816, and 818 and 819, have common characteristics (b and d, respectively), 808 and 810, and different answers. By comparing these pairs of characteristic relationships, two characteristic-based influence factors can be identified, namely, characteristic b-based influence factor 812 corresponding to both answer A 801 and answer B 802 and characteristic d-based influence factor 813 corresponding to both answer B 802 and answer C 803.

Further, as shown, answer relationships can be generated based on the sets of influence factors. Specifically, a first set of influence factors (including the characteristic b-based influence factor 812 and direct influence factor A/B 811) can be used to generate an answer relationship A/B 804 between answer A 801 and answer B 802. Similarly, a second set of influence factors (including characteristic d-based influence factor 813) can be used to generate an answer relationship B/C 805 between answer B 802 and answer C 803. In addition, because there are no influence factors corresponding to both answer A 801 and answer C 803, answer relationship A/C 806 can, in some embodiments, be deemed non-existent or neutral. Once each of the answer relationships 804-806 have been generated, they can be used to evaluate answer sequence 800.

Figure 9:
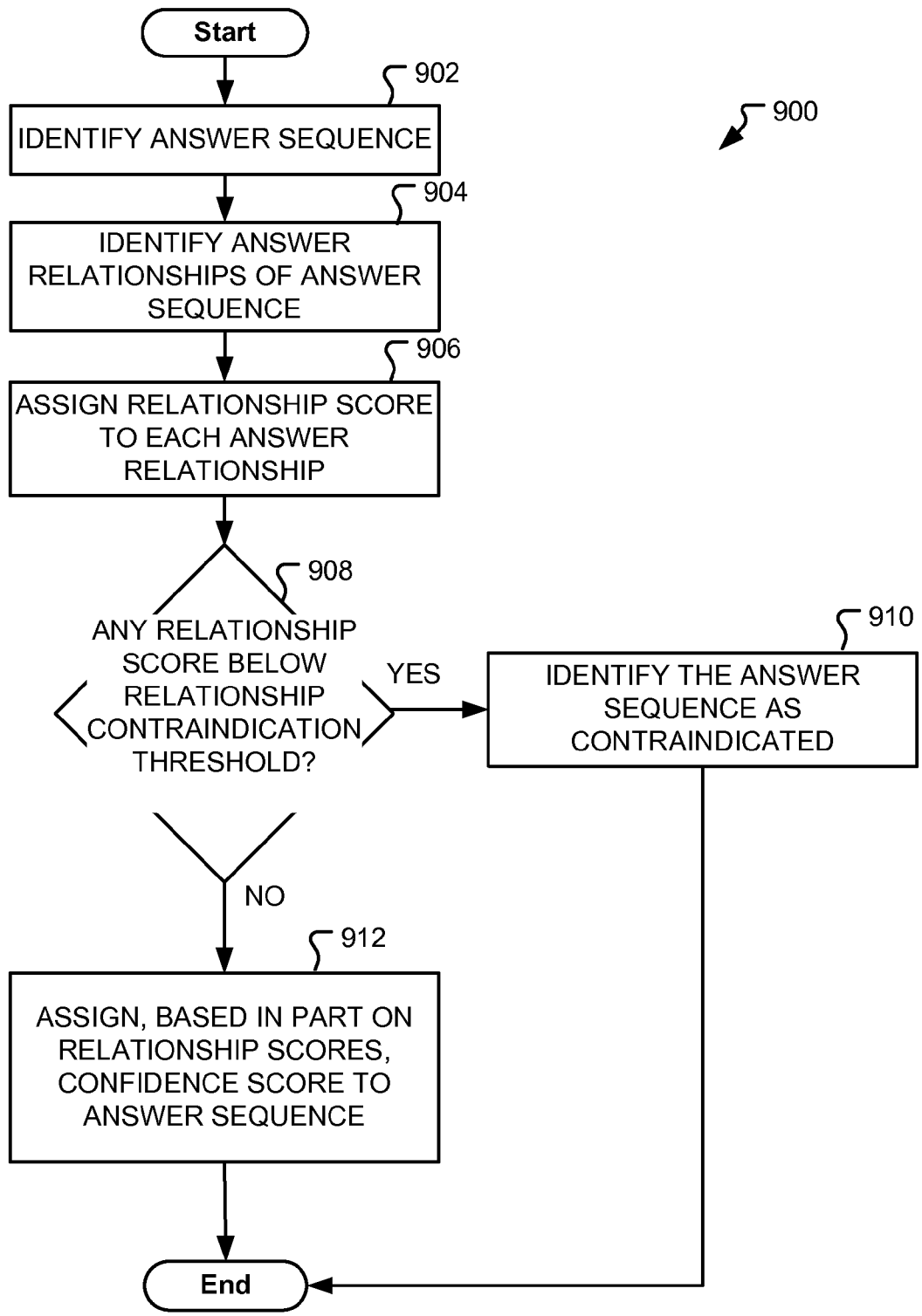
FIG. 9 depicts a flowchart diagram of a method of evaluating an answer sequence based on answer relationships, according to embodiments of the present disclosure.

Referring now to FIG. 9, a flowchart diagram of a method 900 of evaluating an answer sequence based on answer relationships can be seen, according to embodiments of the present disclosure. In operation 902, an answer sequence is identified. In operation 904, answer relationships of the answer sequence can be identified. In some embodiments, operation 904 may involve performing some or all of the operations of method 700 shown in FIG. 7. In operation 906, a relationship score can be assigned to each answer relationship of the answer sequence. As described herein, a relationship score can indicate a measure of the impact that two answers are likely to have on each other or how well they are likely to interact in a given answer sequence. Relationship scores can be positive or negative (e.g., favorable or not favorable). In some embodiments, relationship scores can be based on influence factors. Further, in some embodiments, answer relationship scoring rules may be used to determine relationship scores.

In decision block 908, a determination can be made as to whether there are any relationship scores below a relationship contraindication threshold. As described herein, a relationship contraindication threshold can refer to a minimal acceptable level for a relationship score (e.g., the most negative that a relationship score can be while still being acceptable). If a given relationship score is below this threshold, then the answer sequence with which the given relationship score is associated may be contraindicated. As described herein, an answer sequence may be considered contraindicated when it is deemed unusable or improper as a result of a negative evaluation of an answer relationship for answers of that particular answer sequence. In some embodiments, employing such a threshold can help to ensure that a strongly negative relationship between two answers of an answer sequence can prevent the answer from being recommended to a user. In embodiments, relationship contraindication thresholds can be more tolerant or less tolerant of negative relationship scores. A less tolerant threshold can be applied, for example, in situations where it is more important to be sure that negative interactions between answers of a particular answer sequence are limited if that answer sequence is to be presented to a user (e.g., in a medical treatment setting).

If in operation 908, at least one relationship score is below the threshold, then, in operation 910, the entire answer sequence may be identified as contraindicated. In some embodiments, this contraindication identification may mean that the answer sequence is not even presented to the user as a possible answer sequence; or, in other embodiments, the answer sequence may only be presented along with a warning label and a description of the reason for the contraindication. As an example, consider a generic answer sequence of JKLM. If an answer relationship between L and M has a relationship score below a threshold, then the answer sequence JKLM may be identified as contraindicated even though all of the remaining answer relationships (between J and L, between K and M, etc.) are all associated with relationship scores above the threshold.

If in operation 908, all of the relationship scores are above the relationship contraindication threshold, then, per operation 912, a confidence score can be assigned to the answer sequence. The confidence score can be based in part on the relationship scores associated with the answer sequence. In some embodiments where an original confidence score has been assigned to the answer sequence prior to the answer relationship evaluation, a revised confidence score can be assigned. The revised confidence score can be based on both the original confidence score and the relationship scores.

Figure 10:
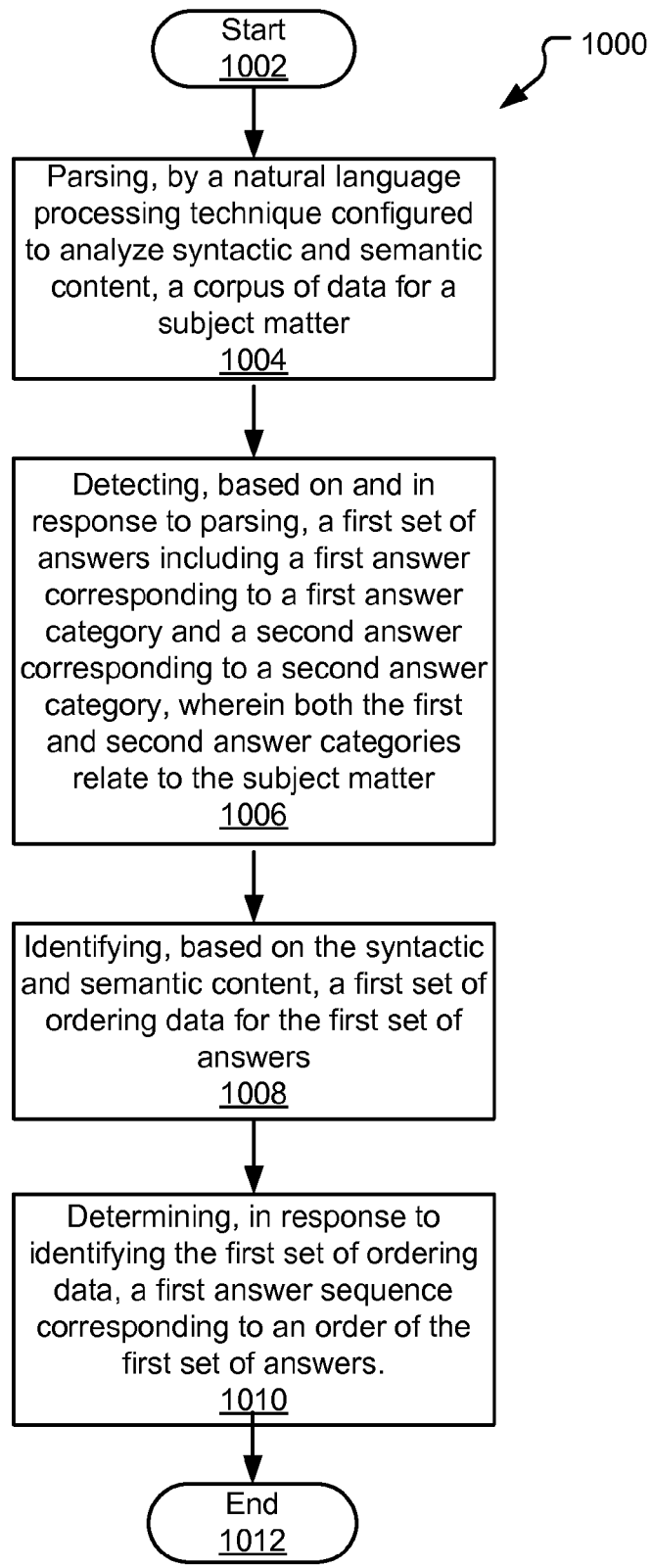
FIG. 10 is a flowchart illustrating a method for managing answer sequences, according to embodiments of the present disclosure.

FIG. 10 is a flowchart illustrating a method 1000 for managing answer sequences, consistent with embodiments of the present disclosure. Aspects of FIG. 10 are directed toward determining a first answer sequence using ordering data for a first set of answers. The method 1000 may begin at block 1002 and end at block 1012. Consistent with various embodiments, the method 1000 may include a parsing block 1004, a detecting block 1006, an identifying block 1008, and a determining block 1010.

Consistent with various embodiments, at block 1004 the method 1000 may include parsing, by a natural language processing technique, a corpus of data for a subject matter. The subject matter may include content or data related to particular topic, theme, or concept. The natural language processing technique may be configured to parse syntactic and semantic data of the corpus of data. In certain embodiments, the corpus of data for the subject matter may be a database including one or more types of content related to a particular topic or subject. The types of content may include, for instance, research results, practice trial results, journal articles, historical data, or the like. For example, in certain embodiments, the database may include medical research trials, journal articles and other sorts of content relating to a subject matter of oncology treatment. As an additional example, the database may include content related to one or more other subjects, such as gardening, computer technical support, or beekeeping. Other subject matters are also possible. In certain embodiments, the subject matter content on the database may be organized, classified, and tagged. For instance, the subject matter content on the database may be organized or structured by linking concepts and subtopics together using an ontology framework. In certain embodiments, the corpus of data may correspond to information corpus 326 of FIG. 3.

As described herein, at block 1004 the method may include parsing the corpus of data for the subject matter using a natural language processing technique. The natural language processing technique may be configured to parse both structured data (e.g., tables, graphs) and unstructured data (e.g., textual content containing words, numbers, dates). In certain embodiments, the natural language processing technique may be a software tool, widget, or other program configured to analyze and identify the semantic and syntactic elements and relationships present in the corpus of data. More particularly, the natural language processing technique can be configured to parse the grammatical constituents, parts of speech, context, and other relationships (e.g., modifiers) of the corpus of data. The natural language processing technique can be configured to recognize keywords, contextual information, and metadata tags associated with words, phrases, or sentences in the corpus of data. In certain embodiments, the natural language processing technique can analyze summary information, keywords, figure captions, or text descriptions included in the corpus of data, and identify syntactic and semantic elements present in this information. The syntactic and semantic elements can include information such as word frequency, word meanings, text font, italics, hyperlinks, proper names, noun phrases, parts-of-speech, or the context of surrounding words. Other syntactic and semantic elements are also possible.

In certain embodiments, at block 1006 the method 1000 may include detecting, based on the parsing, a first set of answers and a second set of answers. The first set of answers may include a first answer belonging to a first answer category and a second set of answers belonging to a second answer category. In certain embodiments, both the first and second answer categories may correspond to the subject matter. Generally, an answer (e.g., first answer, second answer) may refer to a data object or concept that may be returned in response to a query (e.g., a question in a question-answering system). In certain embodiments, the answer may correspond to a particular noun, entity, operation, or action. For example, in response to a question asking for the name of the national bird, the answer may be returned as "bald eagle. In certain embodiments, the answer may correspond to an answer category. The answer category may be a division or class of concepts or ideas that include the answer. For instance, the answer of "bald eagle" may correspond to an answer category of "birds." Additionally, each answer category may correspond to a subject matter. As described herein, the subject matter may be content or data related to particular topic, theme, or concept, and may include the answer category. As an example, referring to the example above, the answer category of "birds" may be related to a subject matter of "animals," "wildlife," or the like.

As described herein, at block 1006 the method 1000 can include detecting a first set of answers and a second set of answers based on parsing a corpus of content related to a subject matter. In certain embodiments, the first and second set of answers may be detected by the natural language processing system. For example, the natural language processing may determine the words, phrases, or data present in the corpus that corresponds to the question received by a question answering system. The answers may be tagged or marked with an identifier to indicate correspondence to the question. As an example, in certain embodiments the question answering system may receive a question related to treatment options for a particular medical condition. The answers to the question may include a variety of medical treatments. The medical treatments may correspond to specific categories (e.g., answer categories) that represent a larger group of treatments. More specifically, the method 1000 may include detecting a first set of answers including a first answer of "antimetabolites" and a second answer of "cryosurgery." The first answer may correspond to a first answer category of "chemotherapy," and the second answer may correspond to a second answer category of "surgery." Both the first and second answer categories may correspond to a subject matter such as "cancer treatments." Other types of answers and answer categories are also possible.

Consistent with various embodiments, at block 1008 the method 1000 may include identifying, based on the syntactic and semantic content, a first set of ordering data for the first set of answers. The first set of ordering data may be structured or unstructured data or information that suggests (e.g., explicitly or implicitly) a particular order or sequence for the first answer and the second answer. The first set of ordering data may be identified using the syntactic content of the corpus of data, the semantic content of the corpus of data, or both. As an example, in certain embodiments, the ordering data may be a table that specifies a sequence of steps in which certain processes are performed. In certain embodiments, the ordering data may be extracted from textual content of the corpus of data. For instance, the corpus of data may state a date or day of the week that a first step was performed, and another date or day of the week that a second step was performed. Using the included date or day of the week, the natural language processing could determine the order of the first step and the second step. Additionally, the method 1000 may identify keywords such as "first," "after," "before," "last," and other words that may indicate a temporal order. As described herein, the natural language processing technique can be configured to identify the ordering data from both unstructured and structured data environments.

As an example, consider the following paragraph, which may be a message board post returned in response to a query related to fixing a computer:

> In order to fix my laptop, I had to reinstall the operating system. Prior to that, however, I backed up all of my data to a large external hard drive, and then proceeded to format the internal hard drive of my laptop. Then I made a partition on the freshly-formatted hard drive for the new OS. After restarting the system and changing the boot priority to boot from the DVD drive, I put in my OS CD, restarted the system again, and followed the instructions to reinstall the operating system. Then I replaced my backed-up data onto my laptop hard drive, and before I knew it, it was operating like it was brand new.

As described herein, the method 1000 may detect answers including "Data backup," "Hard drive format," "Hard drive partition," "System Restart," "Change Boot Priority," "OS CD Insertion," "System Restart," "OS Installation Process," and "Data Replacement." At block 1008 the method 1000 can identify ordering data in the form of temporal keywords such as "after," "before," "then," "prior," "proceeded to" as well as other ordering data that suggests a sequence for the detected answers. In certain embodiments, the method 1000 can include marking the identified ordering data with special tags or identifiers. For example, the method 1000 may include highlighting the identified ordering data, or attaching a tag to each instance of ordering data. In certain embodiments, the method 1000 may be configured to provide an ordering data report indicating the identified ordering data in a particular corpus of data (e.g., it may be desirable for a user to see the factors that influenced the order for a particular set of answers).

Consistent with various embodiments, at block 1010 the method 1000 can include determining, in response to identifying the first set of ordering data, a first answer sequence corresponding to an order of the first set of answers. The first answer sequence may be an arrangement, succession, or series of one or more answers (e.g., the first set of answers and the second set of answers). The arrangement of the answers in the first answer sequence may be associated with positive impacts (e.g., performance and efficiency benefits) in comparison to other orders or configurations of the answers. As described herein, in certain embodiments, the first answer sequence may be determined using the first set of ordering data identified for the first set of answers. For instance, referring to the example above, the identified ordering data such as the temporal keywords "after," "before," "then," "prior," and "proceeded to" may be used to determine a first answer sequence of "Hard drive format-Hard drive partition-System Restart-Change Boot Priority-OS CD Insertion-System Restart-OS Installation Process-Data Replacement."

In certain embodiments, the method 1000 may include determining a second answer sequence. In certain embodiments, the second answer sequence may be determined based on a second corpus of data different than the corpus of data used to identify the first answer sequence. In certain embodiments, the first and second answer sequences may be determined using the same corpus of data. More particularly, the method 1000 may include detecting a third set of answers including a third answer corresponding to a third answer category, a fourth set of answers including a fourth answer corresponding to a fourth answer category, and a fifth set of answers including a fifth answer corresponding to a fifth answer category. In certain embodiments, the third, fourth, and fifth answer categories may relate to the subject matter. Based on syntactic and semantic content, the method 1000 may include identifying a second set of ordering data for the third, fourth, and fifth sets of answers. In response to identifying the second set of ordering data, the method 1000 may include determining a second answer sequence corresponding to an order of the third, fourth, and fifth sets of answers.

In certain embodiments, the method 1000 may include establishing a sentiment factor for an answer sequence. The sentiment factor may be an integer value between 1 and 100 that represents the relative sentiment (e.g., attitude, position, opinion, emotions) associated with an answer sequence. As described herein, the sentiment factor for an answer sequence may be determined based on an analysis of the contextual information, linguistic data, and semantic elements associated with a particular answer sequence. As an example, an answer sequence that includes words and phrases such as "ineffective," "poor performance," and "problematic" may be characterized as having a substantially negative sentiment, while an answer sequence that is associated with words and phrases such as "exceedingly efficient," "effective" and "favorable outcome" may be characterized as having a substantially positive sentiment. As described herein, in certain embodiments, the natural language processing technique may determine a sentiment factor for the first and second answer sequence. The sentiment factor may be an integer value that characterizes the attitude or emotions of the corpus of data with respect to the answer sequence. For instance, as described herein, the sentiment factor may be an integer value between 1 and 100, wherein lower integers indicate a generally lower (e.g., substantially negative, or unfavorable) sentiment, and higher integers indicate a generally higher (e.g., substantially positive, or favorable) sentiment.

In certain embodiments, the method 1000 may include comparing the first answer sequence and the second answer sequence based on the first sentiment factor and the second sentiment factor. For example, consider a scenario in which the first answer sequence has a first sentiment factor of 76, and the second answer sequence has a second sentiment factor of 53. In response to comparing the first and second sentiment factors, the method 1000 may include rank-ordering (e.g., ranking, organizing, classifying) the first and second answer sequences based on the comparison of the first and second sentiment factors. For instance, in certain embodiments, the method 1000 could include ranking the first answer sequence (e.g., the answer sequence with the greater sentiment factor) above the second answer sequence (e.g., the answer sequence with the lesser sentiment factor). Such an embodiment may provide benefits associated with identifying the answer sequence associated with the most positive results. Other methods of ranking the first and second answer sequences are also possible.

Figure 11:
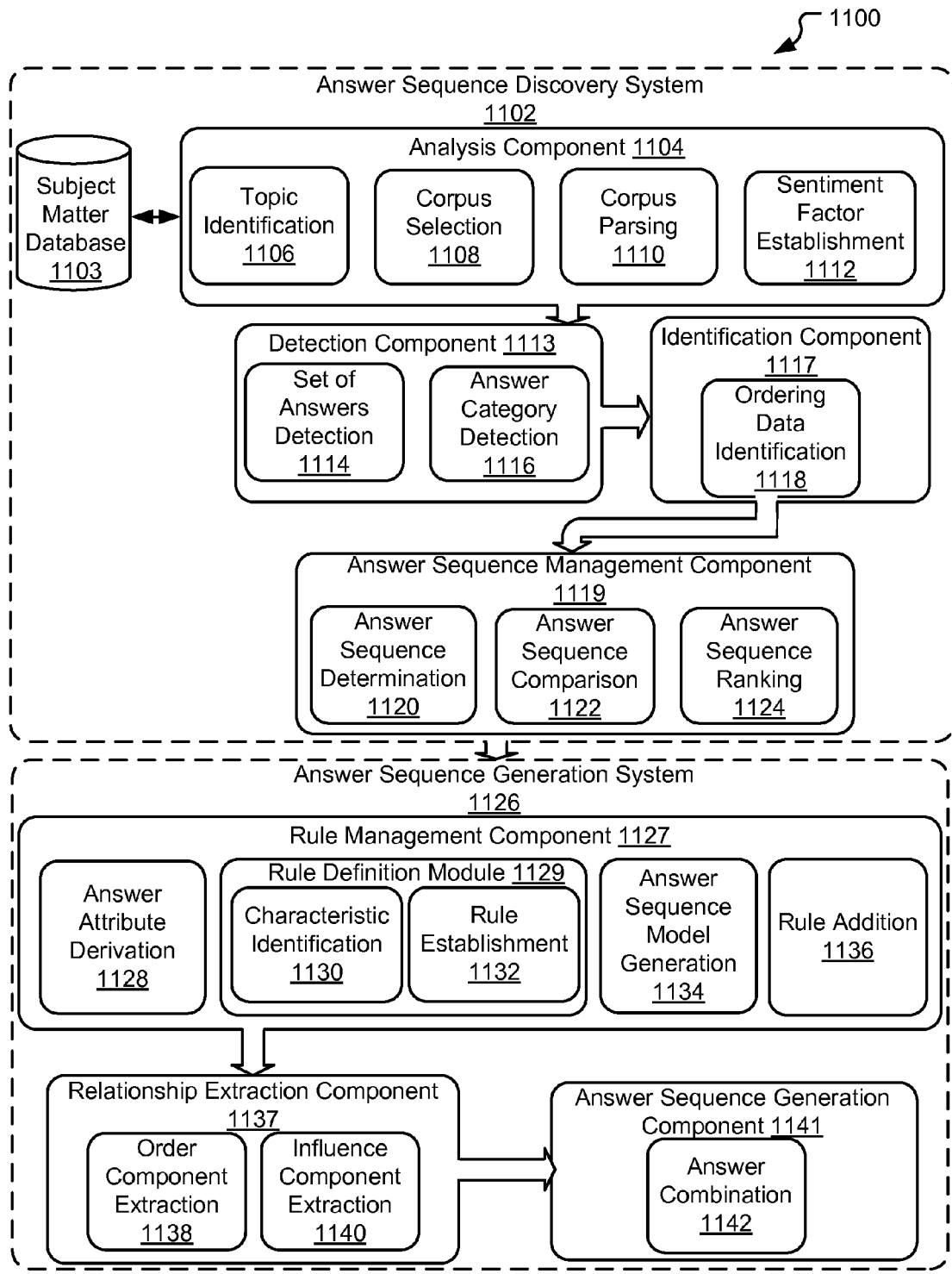
FIG. 11 is a diagram illustrating an example system architecture for managing answer sequences, according to embodiments of the present disclosure.

FIG. 11 is a diagram illustrating an example system architecture 1100 for managing answer sequences, consistent with embodiments of the present disclosure. Aspects of FIG. 11 are directed toward an answer sequence discovery system for determining an answer sequence for one or more answers, and using the discovered answer sequences to generate undiscovered answer sequences using an answer sequence module. As shown in FIG. 11, in certain embodiments, the example system architecture 1100 can include an answer sequence discovery system 1102 and an answer sequence generation system 1126. The answer sequence discovery system 1102 can include a subject matter database 1104, an analysis component 1104, a topic identification module 1106, a corpus selection module 1108, a corpus parsing module 1110, a sentiment factor establishment module 1112, a detection component 1113, a set of answers detection module 1114, an answer category detection module 1116, an identification component 1117, an ordering data identification module 1118, an answer sequence management component 1119, an answer sequence determination module 1120, an answer sequence comparison module 1122, and an answer sequence ranking module 1124. The answer sequence generation system 1126 can include a rule management component 1127, an answer attribute derivation module 1128, a rule definition module 1129 including a characteristic identification sub-module 1130 and a rule establishment sub-module 1132, an answer sequence model generation module 1134, a rule addition module 1136, a relationship extraction component 1137 including an order component extraction module 1138 and an influence component extraction module 1140, an answer sequence generation component 1141 and an answer combination module 1142.

Consistent with various embodiments, the analysis component 1104 may substantially correspond with the parsing block 1004 of FIG. 10. In certain embodiments, the topic identification module 1106 can be configured to determine a topic of a question. The question may be a query, statement, or other input received by a question answering system. As described herein, the topic may be identified using natural language processing techniques. Based on the identified topic of the question, the corpus selection module 1108 can be configured to select a corpus of data for a subject matter. In certain embodiments, the topic of the question may be related to the subject matter. As described herein, the corpus parsing module 1110 may be configured to use a natural language processing technique configured to parse semantic and syntactic content of the corpus of data. The sentiment factor establishment module 1112 may be configured to use the semantic characteristics of the corpus of data to establish a quantitative indication of the relative emotions or attitude associated with a particular answer sequence.

Consistent with various embodiments, the detection component 1113 may substantially correspond with detecting block 1006 of FIG. 10. In certain embodiments, the set of answers detection module 1114 may be configured to detect a first set of answers and a second set of answers (e.g., words, phrases, or data present in the corpus that corresponds to the question) in response to the parsing of the corpus of data performed by the corpus parsing module 1110. Further, in certain embodiments, the answer category detection module 1116 may be configured to detect answer categories (e.g., divisions or classes of concepts or ideas that include a respective set of answers) that correspond to the detected first and second set of answers.

Consistent with various embodiments, the identification component 1117 may substantially correspond with identifying block 1008 of FIG. 10. In certain embodiments, the ordering data identification module 1118 may be configured use the parsed semantic and syntactic content of the corpus of data to identify the ordering data. The ordering data may be structured or unstructured data or information that suggests (e.g., explicitly or implicitly) a particular order or sequence for the first answer and the second answer.

Consistent with various embodiments, the answer sequence management component 1119 may substantially correspond with the determining block 1010 of FIG. 10. In certain embodiments, the answer sequence determination module 1120 may be configured to use the ordering data identified by the ordering data identification module 1118 to determine an answer sequence corresponding to an order of the first set of answers. The answer sequence may be an arrangement, succession, or series of one or more answers (e.g., the first set of answers and the second set of answers). In certain embodiments, the answer sequence determination module 1120 may determine multiple answer sequences corresponding to multiple sets of answers. Accordingly, in such an embodiment, the answer sequence comparison module 1122 can compare the determined answer sequences to one another. In certain embodiments, the determined answer sequences may be compared using a sentiment factor associated with each answer sequence (e.g., the sentiment factor established by the sentiment factor establishment module 1112). Other methods of comparing the answer sequences are also possible. In certain embodiments, the answer sequence ranking module 1124 can be configured to rank-order the compared answer sequences. For example, the answer sequence ranking module 1124 may rank-order the answer sequences based on the sentiment factor associated with each answer sequence (e.g., answer sequences with greater sentiment factors are ranked more prominently). Other methods of rank-ordering the answer sequences are also possible.

As described herein, certain embodiments of the present disclosure are directed toward generating undiscovered answer sequences. In certain embodiments, generating the undiscovered answer sequences may include using an answer sequence module including a set of rules derived from previously discovered answer sequences. Accordingly, in certain embodiments, the system architecture 1100 can include an answer sequence generation system 1126. The answer sequence generation system can include components and modules configured to generate undiscovered answer sequences.

Consistent with various embodiments, the answer sequence generation system 1126 can include a rule management component 1127. The rule management component 1127 may include modules and sub-modules directed toward establishing rules to facilitate the generation of answer sequences. In certain embodiments, the rule management component 1127 may include an answer attribute derivation module 1128. The answer attribute derivation module 1128 may be configured to derive a set of answer attributes for a set of answers. In certain embodiments, the answer attribute derivation module 1128 may derive a first set of answer attributes for a first set of answers, and a second set of answer attributes for a second set of answers. In certain embodiments, deriving the set of answer attributes may include using the characteristic identification module 1130 to identify a group of characteristics for the set of answers that indicate a correspondence between a first answer and the second answer. Put differently, the set of answer attributes may include particular traits or features that are distinctive of a specific answer, and suggest a link between the answer and another answer.

For instance, consider an example in which a user wishes to make additional stock market investments. The set of answers detection module may detect a first answer of "PMJ Oil" and a second answer of "AKB Entertainment." For the first answer of "PMJ Oil" the answer attribute derivation module 1128 may derive a first answer attribute such as "Stock in oil companies is currently under-valued" and a second answer attribute of "Stock in broadcasting and entertainment companies is currently overvalued." As described herein, in certain embodiments, the set of answer attributes may be derived from the semantic and syntactic content parsed by the natural language processing technique (e.g., company financial statements, editorials of industry experts, and the like.)

In certain embodiments, the rule establishment module 132 may be configured to establish rules (e.g. also referred to herein as answer sequence rules) based on the derived attributes/identified characteristics for the first answer and the second answer. Generally, the rules may include principles, guidelines, facts, or indications that can be used to formalize the connection, link, or correspondence between the first answer and the second answer. In certain embodiments, the rules may define a procedure that describes a suggested means of interaction or sequential order for the first answer and the second answer. For instance, once again consider the example above, in which the first answer is "PMJ Oil," and the second answer is "AKB Entertainment." Based on the derived first answer attribute (e.g., Stock in oil companies is currently under-valued) and the second answer attribute (e.g., Stock in broadcasting and entertainment companies is currently overvalued) the rule establishment module 1134 may define a rule (e.g., a first-second rule) such as "Stock in AKB Entertainment should not be purchased before stock in PMJ Oil" (e.g., it is a better financial decision to buy undervalued stock while the price is low, and avoid buying stocks for which the price is overvalued.) In certain embodiments, the rule establishment module 1132 may be configured to define multiple rules based on the derived attributes for the first and second answer. Although the present example was described in terms of a first answer and a second answer, rules generated for situations with greater or fewer answers are also possible.

Consistent with various embodiments, the answer sequence model generation module 1134 may be configured to generate an answer sequence model for managing answer sequences. In certain embodiments, the answer sequence model may be a database or other repository of answer sequences and answer sequence rules. In certain embodiments, the answer sequence model may include using machine learning techniques configured to analyze the answer sequences and answer sequence rules to infer relationships, connections, and other links between various answers, answer categories, and answer sequences. For example, the answer sequence model may include using inference algorithms to extract the connections and links between different answer sequences. In certain embodiments, the links and connections extracted by the inference algorithms may be used to generate additional answer sequences (e.g., undiscovered answer sequences.) In certain embodiments, the rule addition module 1136 may be configured to identify additional rules (e.g., based on a third set of answer attributes for a third answer and a fourth set of answer attributes for a fourth answer) and append them to the answer sequence model. For example, the rule addition module 1136 may be configured to formalize the inferred connections and links between two particular answers, and append them to the answer sequence model generation module 1134 in the form of additional rules.

Consistent with various embodiments, as described herein, the relationship extraction component 1137 may be configured to extract relationships between two or more answer sequences to generate additional answer sequences. Generally, the relationships may be inferred based on attributes or characteristics that are shared between multiple answers or multiple answer sequences. In certain embodiments, the relationships may be formalized as higher-order rules (e.g., broader that the first-order answer sequence rules) or principles that govern the interactions between answers of different answer sequences. In certain embodiments, extracting the relationship may include determining an order component and an influence component of a given answer (e.g., a first answer) with respect to another answer (e.g., a third answer). In certain embodiments, the first answer and the third answer may belong to separate answer sequences.

Generally, the order component may include an attribute or characteristic that suggests or governs (e.g., explicitly or implicitly) a particular order or sequence for the first answer with respect to the third answer. For instance, the order component may suggest that the first answer occur before the third answer. In certain embodiments, the order component may suggest that the first answer occur after the third answer. The influence component may include an attribute or characteristic that indicates the degree of influence, impact, or effect that a particular answer has on another answer. The influence component may, in certain embodiments, be expressed as an integer value between 0 and 100, wherein higher numbers indicate substantially high influence, and lesser numbers indicate substantially little influence. For example, in certain situations, it may be very important that a certain answer in an answer sequence be accompanied by another answer (e.g., a certain treatment must be followed by a particular medicine.) In certain situations, it may be of relatively little importance whether a particular answer is accompanied by another answer (e.g., whether or not sprinkles are included in a brownie recipe.) Accordingly, as described herein, the answer sequence generation component 1141 may be configured to generate an answer sequence using the first answer and the third answer. In certain embodiments, generating the answer sequence may include combining the first answer and the third answer based on the influence component and the order component.

FIG. 12 depicts an example of answer sequence generation 1200, consistent with various embodiments. Aspects of FIG. 12 are directed toward generating undiscovered answer sequences using answer sequence rules defined for established answer sequences. More specifically, the example of answer sequence generation 1200 illustrates an embodiment of the present invention directed toward oncology treatment plans. As shown in FIG. 12, the example of answer sequence generation 1200 may include a set of discovered answer sequences 1202 with a first answer sequence 1210 and a second answer sequence 1220. The example of answer sequence generation 1200 may also include a set of generated answer sequences 1222 with a third answer sequence 1230 and a fourth answer sequence 1240. Each answer sequence may include a set of answers (e.g., Chemotherapy C, Radiation B, etc., wherein Chemotherapy C and Radiation B are specific answers/treatment types within the respective answer categories of "chemotherapy" and "radiation.")

As described herein, the present example may take place within a question-answering system environment. For example, as described herein, in response to a query of "What is the best way to treat cancer for a patient with the provided medical history?" the question-answering system may determine, using a corpus of data including doctor's notes, medical journal articles, and research studies, that the treatment plans of the first answer sequence 1210 and the second answer sequence 1220 are two known treatment plans for patients with the provided medical history. Aspects of the present disclosure are directed toward using an answer sequence generation model equipped with inference algorithms to analyze the first answer sequence and the second answer sequence as well as associated answer sequence rules, and extract relationships that facilitate the generation of additional answer sequences. For instance, based on semantic and syntactic information associated with the first answer sequence (e.g. past medical trials, medical history, oncology journals), a first answer sequence rule such as "Endocrine A may be safely followed by Radiation B," for the first answer sequence. Similarly, a second answer sequence rule such as "Radiation B can be followed by any type of surgery provided that Chemotherapy C is applied immediately afterwards."

Accordingly, as described herein, the answer sequence model may be configured to analyze the first answer sequence rule and the second answer sequence rule, and extract a relationship between the first answer sequence and the second answer sequence in order to generate additional answer sequences. For example, the answer sequence model may combine the first answer sequence rule and the second answer sequence rule to deduce that, as Radiation B can safely be applied after Endocrine A, and any type of surgery can be applied after Radiation B as long as it is followed by Chemotherapy C, that the third answer sequence 1230 and the fourth answer sequence 1240 are also possible. Accordingly, as described herein, the answer sequence model may generate the third answer sequence 1230 and the fourth answer sequence 1240, and add them to a repository or database of known answer sequences.

Figure 13:
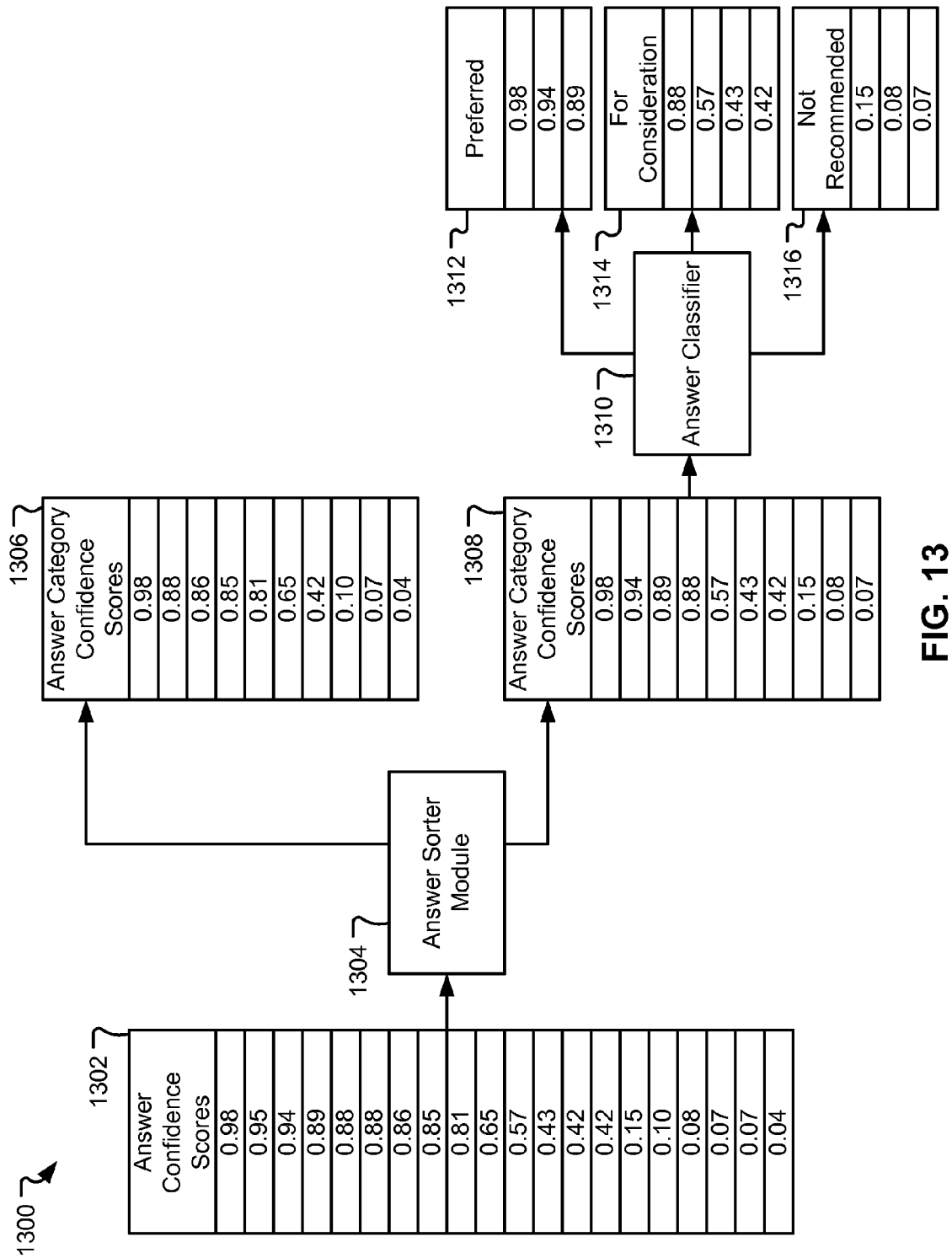
FIG. 13 depicts a conceptual diagram of a QA system configured to classify answers sorted according to answer category, according to embodiments of the present disclosure.

Referring now to FIG. 13, a conceptual diagram illustrating a QA system 1300 that classifies answers sorted according to answer category can be seen, according to embodiments of the present disclosure. The system 1300 can include an answer sorter module 1304 and an answer classifier system 1310.

The answer sorter module 1304 can be the same or substantially similar as the answer sorter system 414 (FIG. 4). The answer sorter module 1304 can be configured to sort answers generated in response to an input query into one or more answer categories. As described herein, the answers can include corresponding answer confidence scores 1302 that represent the QA system's 1300 confidence in each answer generated.

For example, the answer sorter module 1304 can be configured to sort a first set of the answers into a first answer category and a second set of the answers into a second answer category. A set of answer category confidence scores 1306 corresponding to the first set of answers can be sorted into the first answer category. A set of answer category confidence scores 1308 corresponding to the second set of answers can be sorted into the second answer category.

The answer classifier system can be configured to manage confidence data in the QA system 1300. In embodiments the answer classifier system 1310 can be configured to receive answer category confidence scores 1306, 1308 as inputs. In embodiments, the answer classifier system can be configured to classify confidence scores in the answer category confidence scores into one or more buckets, described further herein. For example, in FIG. 13, answer classifier 1310 can be seen receiving answer category confidence scores 1308 as an input and outputting the confidence scores sorted into one or more buckets 1312, 1314, 1316. Described further herein, the answer classifier 1310 can sort answer category confidence scores using static thresholds and/or dynamic thresholds. Buckets 1312, 1314, 1316 can include one or more confidence scores labeled with a descriptions. For example, in FIG. 13 bucket 1312 is labeled as "preferred", bucket 1314 is labeled as "for consideration" and bucket 1316 is labeled as "not recommended". In embodiments, answer classifier 1310 can be configured to classify answers into buckets based on the answer's corresponding confidence score.

Figure 14:
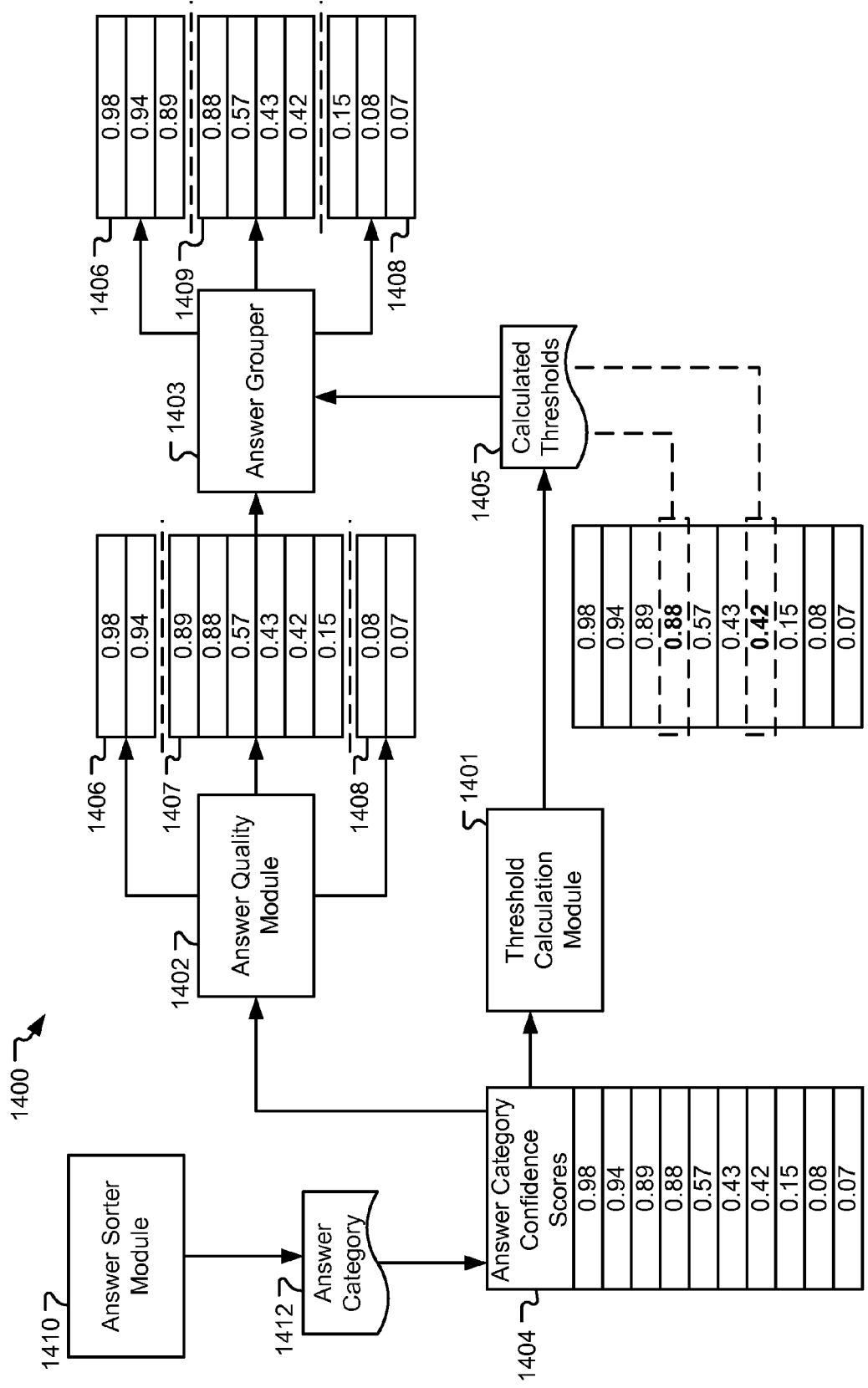
FIG. 14 depicts a conceptual diagram of a QA system configured to classify answers with buckets using multiple sets of thresholds, according to embodiments of the present disclosure.

Referring now to FIG. 14, a conceptual diagram illustrating a QA system 1400 that classifies answers with buckets using multiple sets of thresholds can be seen, according to embodiments of the present disclosure. In embodiments, some or all of the QA system 1400 can be an example implementation of answer classifier 1310 (FIG. 13). FIG. 14 depicts a QA system 1400 including an answer sorter module 1410, a threshold calculation module 1401, an answer quality module 1402, and an answer grouper 1403. As described herein, the answer sorter module 1410 can be configured to sort answers generated in response to an input query into one or more answer categories. As described herein, the answers can include corresponding answer confidence scores 1404 that represent the QA system's 1400 confidence in each answer generated.

As described herein, answers and the corresponding answer confidence scores can serve as an input to the answer sorter module 1410. In embodiments, the answer sorter module 1410 can be the same or substantially similar as the answer sorter system 414 (FIG. 4). The answer sorter module 1410 can be configured to sort answers generated in response to an input query into one or more answer categories such as answer category 1412. Answer category 1412 can be the same or substantially similar as described herein. Answer category 1412 can include a set of answers sorted into the answer category 1412 by the answer sorter module 1410. The set of answers can include a corresponding set of answer category confidence scores 1404 representing the QA system's confidence in each answer in the answer category 1412.

Answer confidence scores 1404 can serve as an input to the threshold calculation module 1401 and the answer quality module 1402. The threshold calculation module 1401 can be configured to calculate thresholds 1405 based on the answer confidence scores 1404. In embodiments, the answer quality module 1402 classifies some of the answer confidence scores 1404 with static thresholds and one or more buckets. The answer confidence scores not classified with a bucket by the answer quality module 1402 are unclassified answer confidence scores 1407. For example, FIG. 14 depicts three buckets, a "preferred" bucket 1406, a "for consideration" bucket 1409, and a "not recommended" bucket 1408. The unclassified answer confidence scores 1407 and the calculated thresholds 1405 serve as inputs into the answer grouper 1403.

The answer quality module 1402 and the threshold calculation module 1401 can be configured to receive the answer confidence scores 1404. The threshold calculation module 1401 and the answer quality module 1402 can receive the answer confidence scores 1404 in parallel or sequentially. In some instances, the answer quality module 1402 and the threshold calculation module 1401 receive the answer confidence scores 1404 from a component of the QA system 1400, such as an answer generator 328 (FIG. 3) that generates the answer confidence scores 1404 and the corresponding answers.

The answer quality module 1402 can be configured to classify answer confidence scores 1404 with a "preferred" bucket 1406 and a "not recommended" bucket 1408 based on static thresholds. Answer confidence scores not classified into the "preferred" bucket 1406 or into the "not recommended" bucket 1408 are unclassified answer confidence scores 1407. For example, the answer quality module 1402 can apply the answer quality thresholds of "0.9" and "0.1"

for the "preferred" bucket 1406 and the "not recommended" bucket 1408, respectively. Therefore, in embodiments, answer confidence scores 1404 above a 0.9 can be placed into the "preferred" bucket 1406, and the answer confidence scores 1404 below 0.1 can be placed into the "not recommended" bucket 1408. In embodiments, the static thresholds are determined before the answer confidence scores 1404 are received. In embodiments, the static thresholds can allow a user to set answer quality thresholds that place certain answer confidence scores into a particular bucket regardless of the value of the calculated thresholds 1405. For example, the static thresholds can override the calculated thresholds 1405, such that the static thresholds prevent the calculated thresholds 1405 from removing some answer confidence scores 1404 from the "preferred" bucket 1406 and/or the "not recommended" bucket 1408.

The static thresholds can identify boundaries between buckets. In some embodiments, the static thresholds can be determined by another component of the QA system 1400. For example, a QA system component could monitor how often users select answers that fall outside of the "preferred" bucket 1406 and adjust the static thresholds accordingly.

The threshold calculation module 1401 can be configured to calculate thresholds 1405. The calculated thresholds 1405 can be calculated in various ways. For example, to calculate the calculated thresholds 1405, the threshold calculation module 1401 can analyze the answer confidence scores 1404. In embodiments, the threshold calculation module 1401 can use a data clustering technique, such as Jenk's natural breaks optimization. In some embodiments, the threshold calculation module 1401 can identify gaps and/or rates of changes associated with the answer confidence scores, described further below. In embodiments, the number of calculated thresholds 1405 is less than the number of buckets used (e.g., one calculated threshold per boundary between buckets). For example, in FIG. 14, a first threshold (0.88) is calculated that distinguishes the "preferred" bucket 1406 from the "for consideration" bucket 1409. A second threshold (0.42) is calculated that distinguishes between the "for consideration" bucket 1409 and the "not recommended" bucket 1408. Thus, because three buckets are used, two thresholds will be calculated. These threshold values can be used by the answer grouper 1403 to classify answers into buckets, described further herein.

In embodiments, the answer grouper 1403 applies the calculated thresholds 1405 to the unclassified answer confidence scores 1407. The answer grouper 1403 can use the calculated thresholds 1405 to determine in which bucket an answer confidence score from the unassociated answer confidence scores 1407 belongs. In embodiments, the answer grouper 1403 compares each of the unassociated answer confidence scores 1407 to the lowest of the calculated thresholds 1405. Thus, the answer grouper 1403 can associate the unassociated answer confidence scores 1407 that are less than the lowest of the calculated thresholds 1405 (0.42 in this example) with the "not recommended" bucket 1408. In embodiments, the answer grouper 1403 then associates the still unassociated answer confidence scores that are less than the next highest calculated threshold 1405 (0.88 in this example) with the "for consideration" bucket 1409. In embodiments, answer confidence scores left over are associated with the "preferred" bucket 1406. In embodiments, the answer confidence scores that the answer grouper 1403 associates with the buckets are in addition to the answer confidence scores previously associated with the buckets by the answer quality module 1402. The answer grouper 1403 can classify answer confidence scores into buckets without regard to the order of the answer confidence scores or the order of the buckets. In embodiments, the answer grouper 1403 can use techniques where answer confidence scores are associated into buckets in an order from least to greatest, from greatest to least, or in other various orders.

As described herein, the answer quality thresholds can override the calculated thresholds 1405. For example, assume that the lower static thresholds used by the answer quality module 1402 was "less than 0.5". The answer quality module 1402 could associate the answer confidence scores 1404 of 0.43, 0.42, 0.15, 0.08, and 0.07 with the "not recommended" bucket 108, despite the fact the answer grouper 1403 could associate values 0.43 and 0.42 with the "for consideration" bucket 1409 based on the calculated thresholds 1405. In some instances, the QA system 1400 can have the calculated thresholds override the answer quality thresholds. For example, if all returned answers have an answer confidence score in the range 0.9 to 1.0, the QA system 1400 could select to have the calculated thresholds override the answer quality thresholds in order to prevent all returned answers from being associated with the "preferred" bucket 106.

Figure 15:
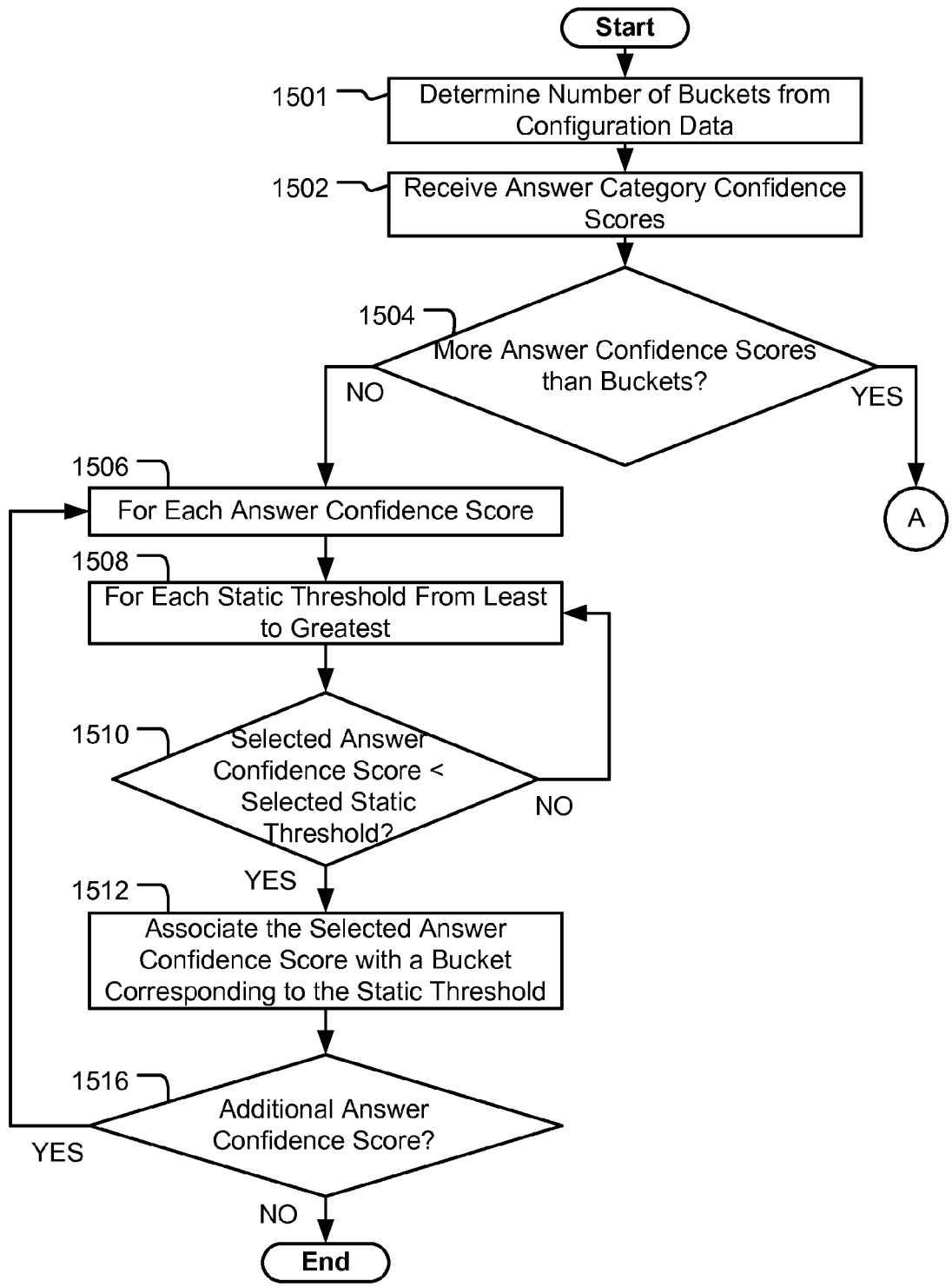
FIG. 15 depicts a flow diagram illustrating example operations for associating answer category confidence scores with confidence buckets, according to embodiments of the present disclosure.

Referring now to FIG. 15 a flow diagram illustrating example operations for associating answer category confidence scores with buckets can be seen, according to embodiments of the present disclosure. At operation 1501, a number of buckets can be determined from configuration data. In embodiments, there are at least two buckets. In some embodiments, the specific number of buckets can vary. For example, it can be determined based on user experiments that a particular number of buckets is optimal for a given scenario or set of scenarios (e.g., for questions from a particular source).

In some instances, too many buckets can reduce the potential benefits of buckets. For example, if there was a bucket for each answer, the buckets might not generate an informative presentation of the answers. Further, system resources, such as processor speed and memory available might impose a practical limit on the number of buckets. The number of buckets might also be variable. For example, the number of buckets might change in proportion to the number of answers determined for a particular query. Once the number of buckets has been determined, control can then flow to operation 1502.

In some embodiments, more thresholds than buckets can be used to create a set of sub-buckets including one or more answer category confidence scores. In embodiments, the set of sub-buckets can then be distributed into buckets according to a user distribution preference.

At operation 1502, a set of answer category confidence scores can be received. As described herein, the set of answer category confidence scores can be confidence scores corresponding to answers sorted into an answer category. As described herein, each answer confidence score can be associated with an answer. The answer confidence scores can be specified in various manners. For example, the answer confidence scores can be specified as percentages (or fractions of 100), integers within a particular range, etc. After the answer confidence scores are received, control can then flow to operation 1504.

At operation 1504, it can be determined whether there are more answer confidence scores than buckets. The number of buckets is the number determined at operation 1501. In embodiments, the number of answer confidence scores is equal to the number of answer confidence scores received in operation 1502. In embodiments, if there are more answer confidence scores than buckets, control can then flow to operation 1618 in FIG. 16. If there are not more answer confidence scores than buckets, control can then flow to operation 1506.

In embodiments, at operation 1506, a loop in which each answer confidence score is iterated over begins. The answer confidence score currently being iterated over can be referred to hereinafter as the "selected answer confidence score". In embodiments, during the first pass through operation 1506, the selected answer confidence score is initialized to a first answer confidence score. On each subsequent pass through operation 1506, the selected answer confidence score can be updated to be the next answer confidence score. In embodiments, the loop continues until all answer confidence scores have been iterated over. In embodiments, after the selected answer confidence score has been initialized or updated, control can then flow to operation 1508.

In embodiments, at operation 1508, a nested loop in which a set of static thresholds is iterated over begins. In embodiments, the static thresholds are iterated over from least to greatest. The current static threshold currently being iterated over can be referred to hereinafter as the "selected static threshold". The static thresholds can be used to distinguish one bucket from another bucket. As described herein, static thresholds can be entered by a user, can be calculated based on the number of buckets, etc. In some embodiments, a different number of buckets than the number determined at operation 1501 can be used. In embodiments, during an initial pass through operation 1508 after operation 1506, the selected static threshold can be initialized to the lowest static threshold. On each subsequent pass through operation 1508, the selected static threshold can be updated to be the next greatest static threshold. In embodiments, the loop continues until the selected answer confidence score is less than the selected static threshold. In embodiments, the loop will reinitialize on each iteration of the loop beginning at operation 1506. After the selected static threshold has been initialized or updated, control can then flow to operation 1510.

In embodiments, at operation 1510, it is determined whether the selected answer confidence score is less than the selected static threshold. For example, the selected answer confidence score is compared to the selected static threshold. If the answer confidence score is not less than the selected static threshold, control can then return to operation 1508. In embodiments, if the answer confidence score is less than the selected static threshold, the nested loop is terminated and control then flows to operation 1512.

In embodiments, at operation 1512, the selected answer confidence score is associated with a bucket corresponding to the selected static threshold. For example, if the nested loop at operation 1508 went through two iterations, then the selected answer confidence score becomes associated with a bucket corresponding to the second greatest static threshold. An answer confidence score can be associated with a bucket by inserting the answer confidence score or a pointer to the answer confidence score into a data structure representing a bucket, inserting in a data structure representing the answer confidence score, an identifier for the associated bucket, etc. Once the selected answer confidence score has been associated with the bucket, control can then flow to operation 1516.

In embodiments, at operation 1516, it is determined whether there is an additional answer confidence score. If there is an additional answer confidence score that has not been associated with a bucket, control can then return to operation 1506. In embodiments, if all answer confidence scores have been associated with a bucket, then the loop beginning at 1506 terminates and the process ends.

Figure 16:
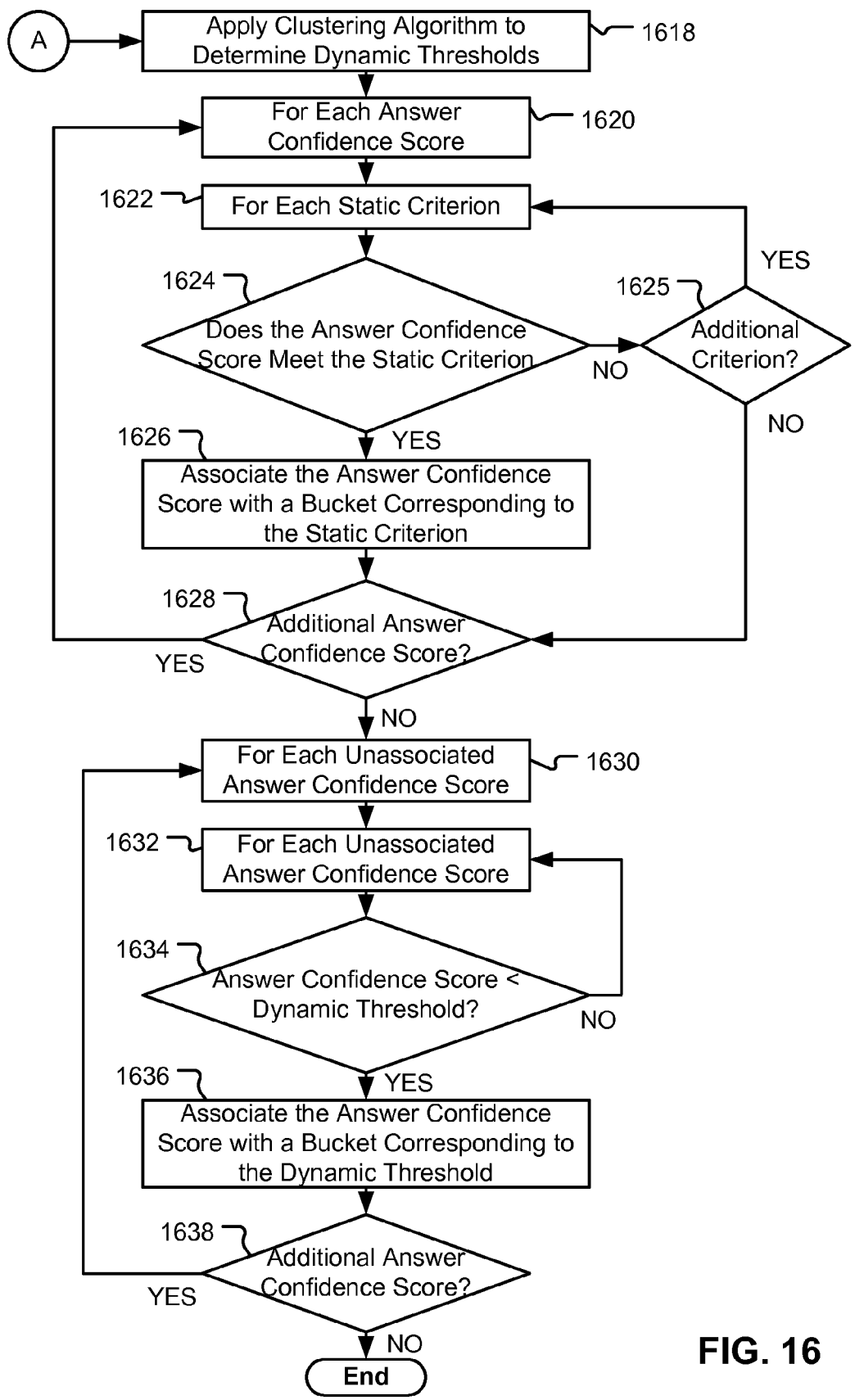
FIG. 16 depicts a flow diagram illustrating example operations for associating answer category confidence scores with confidence buckets, according to embodiments of the present disclosure.

Referring now to FIG. 16, a flow diagram illustrating example operations for associating answers with buckets can be seen, according to embodiments of the present disclosure. In embodiments, control flows to operation 1618 if it was determined, at operation 1504 of FIG. 15, that there are more answer confidence scores than buckets.

In embodiments, at operation 1618, a clustering algorithm can be used to determine dynamic thresholds. The dynamic thresholds can be determined based on the received answer confidence scores and can be different for different sets of answer confidence scores. The dynamic thresholds can be determined in a number of ways. For example, the dynamic thresholds can be determined by using a data clustering technique, such as Jenk's natural breaks optimization. In some examples, the dynamic thresholds can be determined by using techniques that include identifying gaps and/or rates of changes associated with the answer confidence scores.

For example, the size of gaps between answer confidence intervals can be analyzed for gaps over a certain threshold. The size of the gaps can be compared to the standard deviation of all of the gaps, for example. Additionally, the mean variance between answer confidence scores can be calculated, and the gaps can be compared to the mean variance. The answer confidence scores with gaps greater than or equal to the mean variance or the standard deviation can be used as bucket thresholds. In some embodiments, the dynamic thresholds can be determined by determining a plurality of gaps, each gap of the plurality of gaps located between consecutive confidence scores of the confidence scores. Dynamic thresholds can be determined by determining a standard deviation associated with the plurality of gaps and determining that a portion of the plurality of gaps is greater than or equal to the standard deviation. In embodiments, the portion of the plurality of gaps as thresholds.

In some embodiments, dynamic thresholds can be determined by determining a plurality of rate changes. Each rate change of the plurality of rate changes can be a rate change between consecutive confidence scores of the confidence scores. Dynamic thresholds can be determined by determining a portion of the plurality of rate changes to be a largest of the plurality of rate changes. In embodiments, the portion can be used as the dynamic threshold.

In embodiments, the dynamic thresholds are associated with buckets based on the number of buckets and dynamic thresholds. In some embodiments, the dynamic thresholds can be used to define additional buckets.

In embodiments, at operation 1620, a loop in which each answer confidence score is iterated over begins. In embodiments, at operation 1622, a nested loop in which each static criterion is iterated over begins. Answer quality criteria can allow answer confidence scores to be associated with a specific bucket regardless of the other answer confidence scores. Answer quality criteria can be generated by a module of the QA system. In some embodiments, it can be determined from configuration data.

For example, configuration data could indicate that answer confidence scores below 0.3 should be placed in a "not preferred" bucket. Therefore, in embodiments, answer confidence scores less than 0.3 will be placed in the "not preferred" bucket even if the answer confidence score would be associated with a different bucket based on the thresholds determined in operation 1618.

In embodiments, the answer quality criteria can consist of numerical parameters such as ranges or greater than or less than values. In some embodiments, the answer quality criteria can be non-numerical parameters. For example, an answer, in addition to being associated with an answer confidence score, can be associated with other data parameters, such as whether the answer is a known good answer, number of times the answer has been viewed, or amount of evidence supporting the answer. An example of another static criterion is "answers that have been viewed more than 100 times." Meeting such a criterion might result, for example, in an answer confidence score being placed in a "preferred" bucket. Additionally, for example, if an answer is a known good answer, it can automatically be placed in a "preferred" bucket, or, vice versa, a known bad answer in a "not preferred" bucket. Also, a static criterion might be that if an answer is only supported by a small amount of evidence, then it might be associated with a "for consideration" bucket. In embodiments, evidence that supports an answer can be text from a document located in a corpus accessible by the QA system.

In embodiments, at operation 1624, it is determined whether the answer confidence score meets the static criterion. If the answer confidence score does not meet the static criterion, control then flows to operation 1625. In embodiments, if the answer confidence score does meet the static criterion, control then flows to operation 1626.

At operation 1625, it can be determined whether there is an additional static criterion. If there is an additional static criterion, control can return to operation 1622. If each static criterion has been compared to the selected answer confidence score, then the nested loop beginning at operation 1622 terminates and control can then flow to operation 1628.

In embodiments, control can flow to operation 1626 if it was determined, at operation 1624, that the answer confidence score does meet the static criterion. At operation 1626, the answer confidence score can be associated with a bucket corresponding to the static criterion. An answer confidence score can be associated with a bucket by inserting the answer confidence score or a pointer to the answer confidence score into a data structure representing a bucket. In some examples, associating an answer confidence score with a bucket can include inserting an identifier for the associated bucket in a data structure that indicates the answer confidence score. Once the answer confidence score has been associated with the bucket, control can then flow to operation 1628.

In embodiments, control flows to operation 1628 if it was determined, at operation 1625, that there were no additional answer quality criteria. In embodiments, control also flowed to operation 1628 from operation 1626. At operation 1628, it can be determined whether there is an additional answer confidence score. In embodiments, if there is an additional answer confidence score, then control returns to operation 1620. If the answer confidence scores have been evaluated against the answer quality criteria, then the loop beginning at 1620 terminates and control can then flow to operation 1630.

In embodiments, at operation 1630, a loop in which each unassociated answer confidence score is iterated over begins. In embodiments, the unassociated answer confidence scores are those that were not associated with a bucket at operation 1626.

In embodiments, at operation 1632, a nested loop in which each calculated threshold is iterated over begins. The calculated thresholds can be iterated over from least to greatest.

In embodiments, at operation 1634, it is determined whether the unassociated answer confidence score is less than the dynamic threshold. If the unassociated answer confidence score is not less than the dynamic threshold, control can return to operation 1632. If the unassociated answer confidence score is less than the dynamic threshold, the nested loop can be terminated and control then flows to operation 1636.

In embodiments, at operation 1636, the unassociated answer confidence score is associated with a bucket corresponding to the dynamic threshold. For example, if the nested loop at operation 1632 went through two iterations, then the unclassified answer confidence score is associated with a bucket corresponding to the second greatest dynamic threshold. In embodiments, an unassociated answer confidence score can be associated with a bucket by inserting the answer confidence score or a pointer to the answer confidence score into a data structure representing a bucket, inserting in a data structure representing the answer confidence score, an identifier for the associated bucket, etc. In embodiments, once the unassociated answer confidence score has been associated with the bucket, control then flows to operation 1638.

In embodiments, at operation 1638, it is determined whether there is an additional unassociated answer confidence score. If there is an additional unassociated answer confidence score that has not been compared to the dynamic thresholds, control can then return to operation 1630. In embodiments, if all unassociated answer confidence scores have been associated with a bucket, then the loop beginning at 1630 terminates and the process ends.

Figure 17:
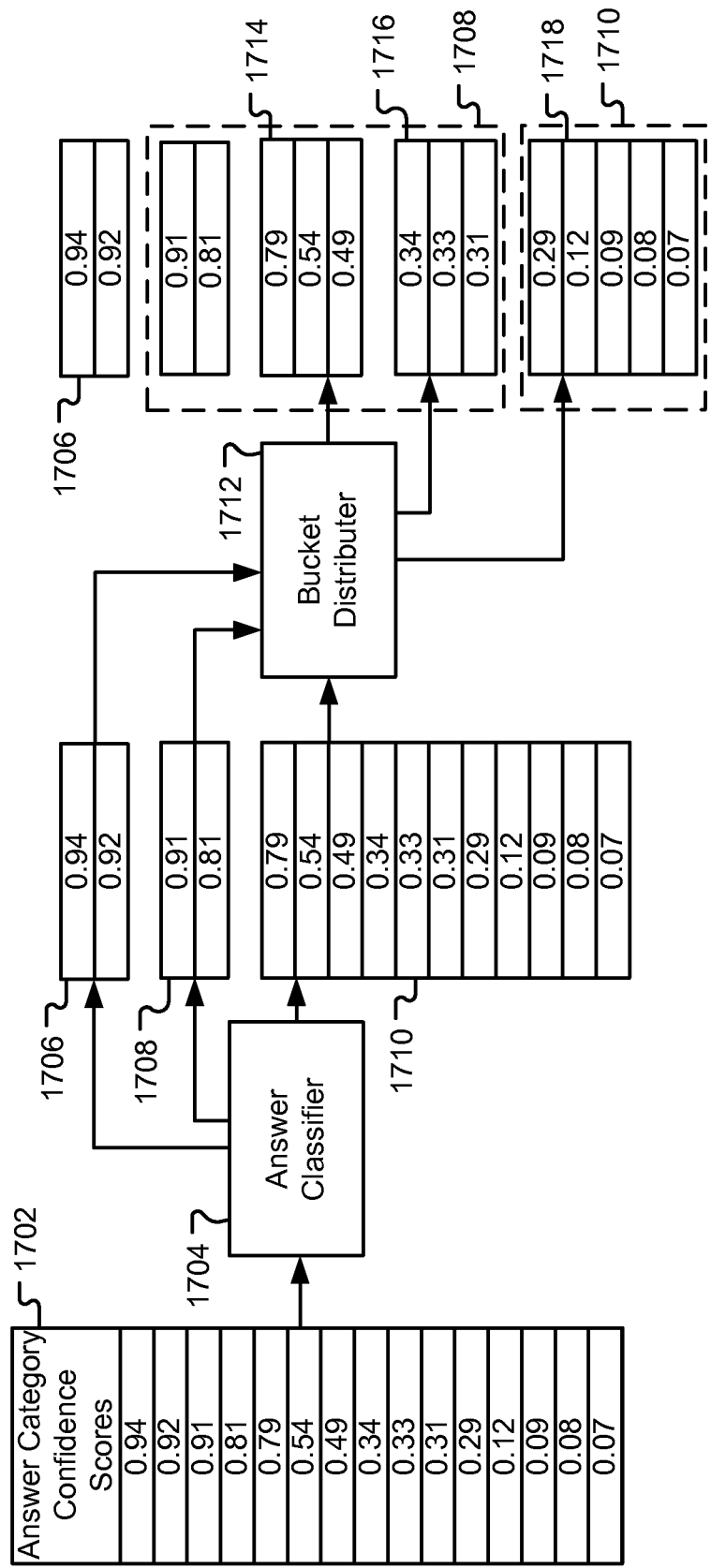
FIG. 17 depicts a conceptual diagram illustrating a QA system configured to distribute answers classified according to confidence buckets, according to embodiments of the present disclosure.

Referring now to FIG. 17, a conceptual diagram illustrating a QA system 1700 that distributes answers classified according to buckets can be seen, according to embodiments of the present disclosure. The system 1700 can include an answer classifier 1704 and a bucket distributer 1712.

Answer classifier 1704 can be configured to receive answer category confidence scores 1702 as an input and output the confidence scores classified into buckets 1706, 1708, 1710. The buckets 1706, 1708, and 1710 can be the same or substantially similar as described herein. As described herein, bucket 1706 could be labeled as a "preferred" bucket, bucket 1708 could be a "for consideration bucket", and bucket 1710 could be a "not recommended" bucket. The answer classifier 1704 can be configured to classify confidence scores into one or more of the buckets using static thresholds and/or dynamic thresholds, as described herein. In embodiments, the answer classifier 1704 can be the same or substantially similar as described herein.

The bucket distributor 1712 can be configured to analyze the buckets 1706, 1708, 1710 and distribute confidence scores among the buckets based on a preferred distribution of confidence scores. As described herein, if too many confidence scores are placed within one or more of the buckets it can reduce the benefits of using buckets to organize the confidence scores. Thus, the bucket distributor 1712 can be configured to redistribute confidence scores among buckets based on the preferred distribution of confidence scores.

In embodiments, the bucket distributor 1712 can be configured to receive the buckets 1706, 1708, 1710 as inputs. The bucket distributor 1712 can be configured to analyze each of the buckets 1706, 1708, 1710 to determine a number of confidence scores sorted into each bucket. The bucket distributor 1712 can be configured to determine whether a number of confidence scores sorted into one or more of the analyzed buckets achieve a distribution threshold. The distribution threshold can be a value representing the percentage of confidence scores in one bucket relative to a total number of the answer category confidence scores 1702. In embodiments, the number of confidence scores achieve the threshold if the number of confidence scores exceeds the distribution threshold. For example, in embodiments, the distribution threshold could be selected as 70%, so that if one of the buckets contains more than 70% of the total number of answer category confidence scores 1702, then the bucket achieves the distribution threshold.

For example bucket distributer 1712 could receive buckets 1706, 1708, and 1710 as an input and determine that bucket 1710 contains eleven confidence scores out of a total of fifteen confidence scores. Thus, bucket distributer 1712 could determine that bucket 1710 contains 73% of the confidence scores and that bucket 1712 achieves a distribution threshold of 70%.

The bucket distributor 1712 can then be configured to redistribute confidence scores in the "large" bucket (the bucket that achieves the distribution threshold) in response to determining that the number of confidence scores achieves the distribution threshold. In embodiments, the bucket distributor 1712 can be configured to perform cluster analysis of the bucket to determine natural breaks within the bucket. In embodiments, the bucket distributor 1712 can perform cluster analysis in the same or substantially similar manner as described herein with reference to the answer classifier 1310 (FIG. 13). For example, in embodiments, bucket 1710 is broken into three sub-buckets 1714, 1716, and 1718 by the bucket distributor 1712.

In embodiments, the bucket distributor 1712 can then be configured to classify the sub-buckets into one or more of the buckets 1706, 1708, and 1710. In embodiments, the bucket distributor 1712 can be configured to promote, demote, or maintain confidence scores in the sub-buckets. In embodiments, the bucket distributor can classify the sub-buckets based on the bucket from which the sub-buckets were formed. In embodiments, the bucket distributor 1712 can move sub-buckets into buckets adjacent from the original bucket. For example, as sub-buckets 1714, 1716, and 1718 were formed from the "not recommended" bucket 1710. Thus, sub-buckets can be promoted to the "for consideration" bucket 1708 or maintained in the "not recommended" bucket 1710. In embodiments, the bucket distributor 1712 cannot remove all confidence scores from the large bucket. For example, in FIG. 17, some confidence scores must be retained in the "not recommended" bucket 1710. Thus, the bucket distributor 1712 can be configured to maintain the third sub-bucket 1718 in the "not recommended" bucket 1710.

In embodiments, the bucket distributor 1712 can be configured to classify the sub-buckets into one or more of the buckets based on a distribution preference. In embodiments, the distribution preference can be a user inputted preference as to which bucket is preferred for confidence scores. For example, if could be preferred that more confidence scores should tend to be included in the "for consideration" bucket 1708 as answers in the "for consideration" bucket 1708 could be more likely to be considered by a user than answers in the "not recommended" bucket 1710.

The bucket distributor 1712 can classify sub-buckets into buckets based on a number of confidence scores that would be in each bucket after classifying and the distribution preference. For example, the bucket distributor 1712 could determine that classifying the second sub-bucket 1716 with the third sub-bucket 1718 would result in the "not recommended" bucket 1710 being larger than the "for consideration" bucket 1708. Further, the bucket distributor 1712 could determine that classifying the first and second sub-buckets 1714, 1716 into the "for consideration" bucket 1708 would result in the "for consideration" bucket 1708 being larger than the "not recommended bucket". Thus, because the bucket distributor 1712 has a distribution preference for the "for consideration" bucket 1708, the bucket distributor 1712 would choose to classify the first and second sub-buckets 1714, 1716 into the "for consideration" bucket 1708.

Figure 18:
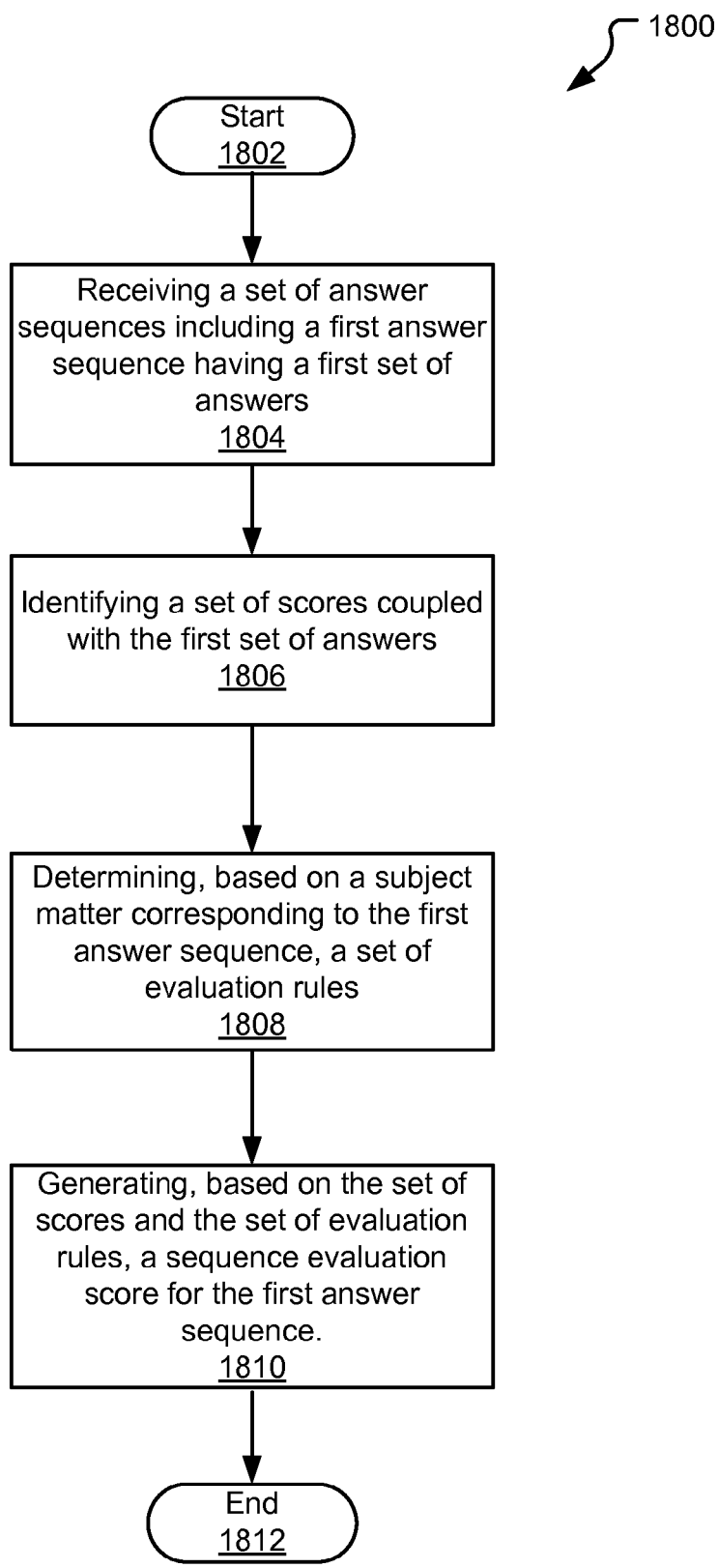
FIG. 18 is a flowchart illustrating a method for scoring answer sequences, according to embodiments.

FIG. 18 is a flowchart illustrating a method 1800 for scoring answer sequences, consistent with embodiments of the present disclosure. Aspects of FIG. 18 are directed toward determining a set of evaluation rules for a first answer sequence, and using the set of evaluation rules to generate a sequence evaluation score for the first answer sequence. The method 1800 may begin at block 1802 and end at block 1812. Consistent with various embodiments, the method 1800 may include a receiving block 1804, an identifying block 1806, a determining block 1808, and a generating block 1810.

Consistent with various embodiments, at block 1804 the method 1800 may include receiving a set of answer sequences including a first answer sequence. As described herein, an answer sequence may be an arrangement, succession, or series of one or more answers (e.g., the first set of answers). The arrangement of the answers in the first answer sequence may be associated with positive impacts (e.g., performance and efficiency benefits) in comparison to other orders or configurations of the answers. In certain embodiments, the set of answer sequences may be received from a user via a visual user interface configured to receive user inputs. For example a user may manually enter a desired answer sequence via the visual user interface, or select one of a set of possible answer sequences. In certain embodiments, the set of answer sequences may be received via one of the methods or systems described herein. For example, in certain embodiments, the method 1800 may receive the set of answer sequences from the answer sequence discovery system 1102 or the answer sequence generation system 1126 of FIG. 11. In certain embodiments, the method 1800 may receive the set of answer sequences in response to determining one or more answer sequences at block 1010 of FIG. 10.

Consistent with various embodiments, at block 1806 the method 1800 can include identifying a set of scores coupled with the first set of answers. Generally, the set of scores can include data such as numbers, letters, or symbols that represent a quantitative indication of the quality, confidence, performance, success, or relevance of a particular answer of the set of answers. For example, in certain embodiments, the set of scores can include confidence scores that represent the reliability of an answer or a set of answers in a question answering system. As described herein, in certain embodiments, the set of scores may be coupled to the first set of answers. More particularly, each answer of the first set of answers may have an associated pre-determined confidence score. In certain embodiments, each answer may have multiple associated scores (e.g., with conditions specifying the circumstances in which a certain score is to be used). Identifying the set of scores may include using a natural language processing technique configured to parse structured and unstructured data associated with the first set of answers, and extracting the set of scores.

Consider the following example. In certain embodiments, the method 1800 may, at block 1804, receive a first answer sequence. As described herein, the first answer sequence may be associated with a subject matter, such as gardening.

Further, in certain embodiments, the first answer sequence may include one or more answer categories. The answer categories may be divisions or classes of concepts or ideas that include one or more answers of the first set of answers. The answer categories may relate to the subject matter of the answer sequence. As an example, in certain embodiments, the first answer sequence may relate to a sequence of steps for growing a bonsai tree. More particularly, the first answer sequence may include answer categories such as "Potting," "Choosing a Location," "Watering," and "Feeding." Within each answer category may be a number of different answers, such as techniques and recommended procedures for each step of the answer sequence. For instance, "Potting" may include answers such as "Pot in the spring," "Pot when the buds extend," and "Pot when the temperature is greater than 76 degrees Fahrenheit," and "Watering" may include answers such as "Water when the top centimeter of soil is dry" and "Water when the roots uncurl." As described herein, each of the answers may have an associated score (e.g. confidence value) that represents the reliability of the answer. In certain embodiments the score may be an integer between 1 and 100, where lower numbers are associated with relatively little reliability, and higher numbers are associated with relatively greater reliability. For instance, the answer of "Pot in the spring," may be associated with a score of 84, "Pot when the buds extend," may be associated with a score of 64, and "Pot when the temperature is greater than 76 degrees Fahrenheit" may be associated with a score of 47. Similarly, "Water when the top centimeter of soil is dry" may be associated with a score of 89, and "Water when the roots uncurl" may be associated with a confidence score of 39.

Consistent with various embodiments, at block 1808 the method 1800 may include determining, based on a subject matter corresponding to the first answer sequence, a set of evaluation rules. As described herein, in certain embodiments, the first answer sequence may correspond to a subject matter. The subject matter may include content or data related to a particular topic, theme, or concept. As examples, the subject matter may relate to $19^{th}$ century literature, semiconductors, haiku, or woodworking. The set of evaluation rules may be a group of established principles, guidelines, or regulations that can be used to assess the set of answers of a particular answer sequence, and determine an overall answer sequence evaluation score for the first answer sequence.

In certain embodiments, determining the set of evaluation rules to generate the sequence evaluation score may be based on the subject matter of the first answer sequence. More particularly, at block 1808 the method 1800 may include selecting one or more sets of evaluation rules based on characteristics of the subject matter that suggest that a certain set of evaluation rules is suitable. For instance, aspects of the present disclosure relate to the recognition that, in certain situations, there may be benefits associated with evaluating an answer sequence for a first subject matter with particular caution (e.g., medical treatments, oncology, investment plans), while answer sequences for other subject matters (baking brownies, sewing scarves) may not need to be evaluated with the same degree of caution. Further, in certain situations, a particular set of evaluation rules may be desirable in scenarios when certain pertinent information regarding the subject matter is available. Accordingly, aspects of the present disclosure are directed toward determining the set of evaluation rules based on characteristics of the subject matter.

Accordingly, in certain embodiments, determining the set of evaluation rules may include computing a caution value for the first answer sequence. In certain embodiments, the caution value may be based on the subject matter. Generally, the caution value may be a quantitative indication of the seriousness, potential for risk, or severity associated with a particular subject matter. In certain embodiments, the caution value may be an integer between 1 and 100, wherein lower numbers indicate a lower degree of caution and higher numbers indicate a greater degree of caution. As described herein, in certain embodiments the caution value may be computed using a natural language processing technique configured to parse semantic and syntactic content associated with the first answer sequence. For instance, in certain embodiments, the natural language processing technique may be configured to parse a corpus of subject matter data relating to the first answer sequence. In certain embodiments, computing the caution value may include using the natural language processing technique to identify words that indicate that a particular degree of caution be used when considering a given answer sequence (e.g., "risk," "danger," "accident," "careful," "heed," "surgery," "injury," "serious," "threat," "hazard," "cancer.") Further, in certain embodiments, the method 1800 may include comparing semantic content for the first answer sequence with an ontology framework of structured relationships in order to identify particular subject matters that have been flagged as "serious" (e.g., oncology, surgery, investments, severe weather). Other methods of computing the caution value are also possible.

In certain embodiments, in response to computing the caution value for the first answer sequence, the method 1800 may include comparing the caution value to a first caution threshold. The first caution threshold may be a predetermined caution value that, when exceeded, prompts the selection of a first evaluation rule. As an example, in certain embodiments, the first caution threshold may be 64. Accordingly, a first answer sequence with a computed caution value of 67 achieves the first caution threshold of 64, and may prompt selection of the first evaluation rule.

In certain embodiments, the first evaluation rule may include identifying a first score of the set of scores coupled with the first set of answers. In certain embodiments, the first score may not achieve (e.g., be below) a first score threshold. As an example, in certain embodiments, the scores associated with the first set of answers may be distributed into score quintiles, with each quintile representing 20% of the score range associated with the first set of answers. For instance, for a first answer sequence having four answers with scores of 0, 34, 51, and 100, score quintiles may be created to cover score ranges from 1-20, 21-40, 41-60, 61-80, and 81-100. In certain embodiments, the first score threshold may be a value corresponding to 20% of the lowest quintile. In certain embodiments, the first score threshold may be 1% of the lowest quintile. Other methods of setting the first score threshold are also possible. In certain embodiments, the first score threshold may be 5% greater than the lowest score included in the first set of answers. Accordingly, as described herein, at block 1810 the method 1800 can include assigning the first score to the first answer sequence as the sequence evaluation score. Aspects of the present disclosure, in certain embodiments, are directed toward selecting the lowest score of the set of scores, and assigning it to the first answer sequence as the sequence evaluation score. Such a configuration may be associated with benefits such as providing (e.g., to a user) a conservative outlook for the first answer sequence.

As described herein, aspects of the present disclosure are directed toward selecting a second of evaluation rule to evaluate the first answer sequence. In certain embodiments, the second evaluation rule may be selected in response to determining that the caution value for the first answer sequence does not achieve a second caution threshold. As described herein, the second caution threshold may be a predetermined caution value that, when exceeded, prompts the selection of the second evaluation rule. In certain embodiments, the second confidence threshold may be equal to the first confidence threshold. Determining that the caution value does not achieve the second caution threshold may include comparing the caution value to the second caution threshold. As an example, in a situation where the second caution threshold is 71, a caution value of 44 may fail to achieve the second caution threshold.

In response to determining that the caution value does not achieve the second caution threshold, the method 1800 may include selecting a second evaluation rule. In certain embodiments, the second evaluation rule may include calculating an aggregate score for the first answer sequence based on the first set of scores. Generally, the aggregate score may be a cumulative or composite score generated using the first set of scores. For instance, the aggregate score may be calculated using a statistical algorithm such as contra-harmonic mean algorithms, quadratic mean algorithms, arithmetic mean algorithms, geometric mean algorithms, and the like. As a basic example, for a first answer sequence with a set of scores including 38, 27, 95, and 74, the method 1800 may include using a contra-harmonic mean algorithm to generate an aggregate score of 71.3 for the first answer sequence. In embodiments, the method 1800 may include calculating an arithmetic mean of 58.5. Other algorithms and other methods of calculating the aggregate score are also possible. Accordingly, as described herein, aspects of the present disclosure are directed toward calculating the aggregate score and assigning it to the first answer sequence as the sequence evaluation score (e.g., at block 1810 of method 1800). Such a configuration may be associated with benefits such as providing an inclusive, overall summary of the reliability of the first answer sequence.

In certain embodiments, aspects of the present disclosure are directed toward selecting a third evaluation rule to evaluate the first answer sequence. Aspects of the third evaluation rule are directed toward providing a comprehensive, refined evaluation of the first answer sequence. Accordingly, in certain embodiments, aspects of the present disclosure are directed toward identifying a set of answer categories corresponding to the set of answers of the first answer sequence. As described herein, the set of answer categories may be divisions or classes of concepts or ideas that include one or more answers of a set of answers. In certain embodiments, the set of answer categories may relate to a subject matter of an answer sequence. For example, for a subject matter of "oncology," the method 1800 may include identifying answer categories of "endocrine," "chemotherapy," "radiation," and "surgery." As described herein, the answer categories may be identified using a natural language processing technique, and substantially correspond to block 1006 of FIG. 11.

In certain embodiments, in response to identifying the set of categories corresponding to the set of answers of the first answer sequence, the method 1800 may include collecting context data for the set of categories. The context data may indicate a relative importance of a first answer category of the set of answer categories to the first answer sequence as a whole. The context data may also indicate the relative importance of the first answer category in relation to the other answer categories of the set of answer categories. Generally, the context data may include a corpus of textual, video, audio, or other data that provides information relating to the background and additional explanation, elaboration, or details regarding a particular answer category. As an example, once again referring to the example above regarding growing bonsai trees with answer categories of "Potting," "Choosing a Location," "Watering," and "Feeding," the method 1800 may include identifying context information such as bonsai growing guides, journal articles in botanical magazines, and user created video content pertaining to bonsai trees. Other types of context data are also possible.

In certain embodiments, the method 1800 may include evaluating the collected context data. For instance, in certain embodiments, the context data may be evaluated by using a natural language processing technique configured to parse semantic and syntactic content of the context data. Evaluating the context data may include assessing the content of the context data, and ascertaining the usefulness of the context data with respect to the first answer sequence. More particularly, evaluating the context data can include determining that the context data achieves a satisfaction criterion. The satisfaction criterion may, in certain embodiments, be a standard or benchmark to gauge the relative quality or relevance of the collected context data. For instance, satisfaction criterion, in certain embodiments, may include a stipulation that the context data include mention of a relation to either the subject matter of the answer sequence, another answer category of the answer sequence, or both in order to achieve the satisfaction criterion. Accordingly, a journal article (e.g., context data) that includes a sentence such as "It is agreed upon by most experts that careful watering techniques are the single most important factor in raising a healthy bonsai" may be determined to achieve the satisfaction criterion (e.g., mention of "raising a healthy bonsai" is substantially similar to the subject matter of the answer sequence.) Additionally, a journal article that includes a sentence such as "While important, potting and repotting a bonsai is not as crucial to the health of a bonsai as is choosing a suitable location for it," may also be determined to achieve the satisfaction criterion (e.g., a relation between the answer categories of "potting" and "choosing a location" was mentioned.) Other possible satisfaction criteria are also possible.

Accordingly, aspects of the present disclosure, in certain embodiments, are directed toward selecting a third evaluation rule in response to determining that the context data achieves the satisfaction criterion. As described herein, aspects of the third evaluation rule may be directed toward providing a comprehensive evaluation of the first answer sequence by making use of the context data for each answer category. In certain embodiments, the third evaluation rule may include assigning, based on the context data, a weighting value to each answer category of the set of answer categories. For instance, for an answer sequence having two answer categories, the third rule may include assigning a first weighting value to a first answer category and a second weighting value to the second answer category. Generally, the weighting value may be a factor that provides a quantitative representation of the magnitude, impact, or significance of a particular category in relation to the other answer categories of the answer sequence or the answer sequence as a whole. The weighting value may be assigned to each category of the answer categories using information that was present in the context data. The weighting value may, in certain embodiments, be an integer between 0 and 10. For example, referring once again to the example above related to growing a bonsai tree, the answer category of "Potting" may be assigned a weighting value of 4, and the answer category of "Choosing a Location" may be assigned a weighting value of 7 (e.g., the context data indicated that the answer category of "Choosing a Location" was more significant than was the answer category of "Potting.")

Accordingly, in response to assigning weighting values to each answer category of an answer sequence, the method 1800 may include calculating an aggregate score for the answer sequence using the individual weighting values for each respective answer category. As described herein, calculating the aggregate score for the answer sequence may use a statistical algorithm or other technique, such as a contra-harmonic mean technique, a geometric-arithmetic mean technique, or the like.

Consistent with various embodiments, at block 1810 the method 1800 can include generating, based on the set of scores and the set of evaluation rules, a sequence evaluation score for the first answer sequence. As described herein, the sequence evaluation score may represent an overall assessment of the reliability or confidence of the first answer sequence, and may be calculated and assigned to the first answer sequence using one or more of a set of evaluation rules. Although reference is made herein to selecting a particular evaluation rule, embodiments combining multiple evaluation rules, including those not disclosed explicitly herein, are also possible.

Figure 19:
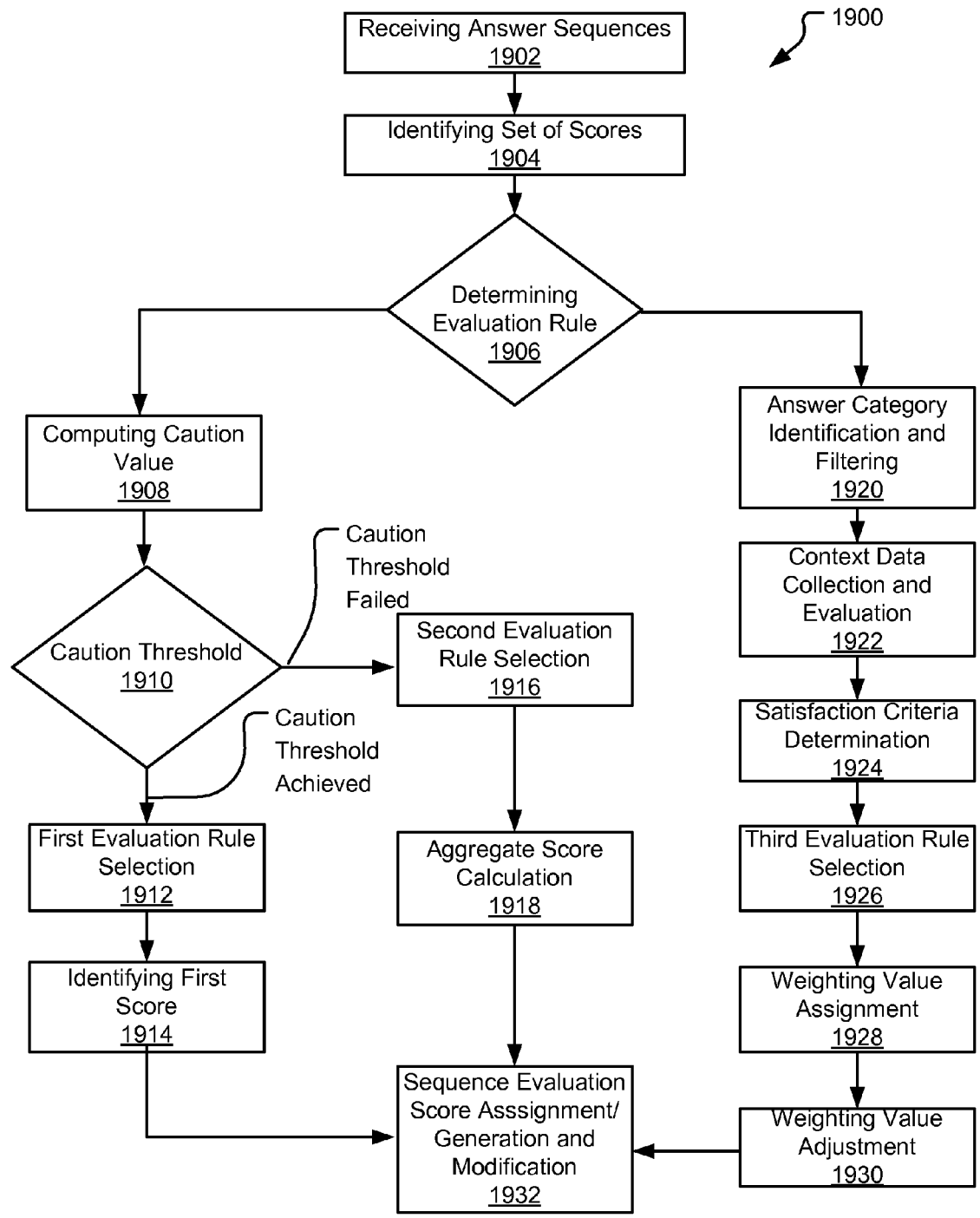
FIG. 19 is a high level flow-diagram of a method for scoring answer sequences, according to embodiments.

FIG. 19 is a high level flow-diagram of a method 1900 for scoring answer sequences, according to embodiments. Aspects of FIG. 19 are directed toward determining (e.g., selecting) an evaluation rule, and using it to calculate and assign a sequence evaluation score to a first answer sequence. As shown in FIG. 19, the method 1900 may, at block 1902, receive answer sequences. Receiving the answer sequences at block 1902 may substantially correspond with receiving block 1804 of the method 1800. At block 1904 the method 1900 may include identifying a set of scores (e.g., confidence values) for an answer sequence. Identifying the set of scores at block 1904 may substantially correspond with block 1806 of the method 1800.

At block 1906, aspects of the present disclosure are directed toward determining an evaluation rule. As described herein, determining the evaluation rule for a particular answer sequence may depend on the characteristics of the subject matter and the information available regarding the answer sequence and the answer categories it includes. In certain embodiments, when a substantial amount of information regarding the answer sequence and the answer categories are available, the third evaluation rule may be chosen. In embodiments where less information regarding the answer sequence and the answer categories are available, the first or second evaluation rules may be chosen. Combinations of the evaluation rules, as well as other evaluations rules, are also possible.

At block 1908, aspects of the present disclosure are directed toward computing a caution value based on the subject matter for the answer sequence. The caution value may be a quantitative indication of the seriousness, potential for risk, or severity associated with a particular subject matter. At the caution threshold decision block 1910, the caution value may be compared to a caution threshold. If the caution value is greater than the caution threshold, the first evaluation rule may be selected at block 1912. If the caution value is less than the caution threshold, the second evaluation rule may be selected at block 1916.

As described herein, in response to selecting the first evaluation rule at block 1912, at block 1914 aspects of the present disclosure are directed toward applying the first evaluation rule and identifying a first score of the set of scores associated with the set of answers of the answer sequence. In certain embodiments, the first score may be below a first score threshold. In embodiments, the first score may be the lowest score of the set of scores. Accordingly, in response to selecting the first score, at block 1932 the first score may be assigned to the answer sequence.

As described herein, if the caution value does not achieve the caution value threshold, aspects of the present disclosure are directed toward selecting the second evaluation rule at block 1916. At block 1918, the second evaluation rule may be applied, and an aggregate score may be calculated for the answer sequence. The aggregate score may be a cumulative or composite score generated using the first set of scores. For instance, the aggregate score may be calculated using an arithmetic-geometric mean technique, arithmetic mean-technique, contra-harmonic mean technique, or other statistical algorithm using the first set of scores. Accordingly, in response to calculating the aggregate score, at block 1932 the aggregate score may be assigned to the answer sequence.

At block 1920, aspects of the present disclosure are directed toward identifying and filtering a set of answer categories for the answer sequence. The answer categories may be divisions or classes of concepts or ideas that include one or more answers of the first set of answers. The answer categories may relate to the subject matter of the answer sequence. In certain embodiments, the answer categories may be filtered from the answer sequence. For instance, at block 1920 the score of each answer of the set of answer categories may be compared to a score threshold, and answer categories that do not include an answer that achieves the score threshold may be removed from the answer sequence. Accordingly, such a configuration may be associated with benefits such as providing reliable and confident answer sequences (e.g., a poor answer or answer category may drag down an otherwise good answer sequence.)

At block 1922, aspects of the present disclosure are directed toward collecting and evaluating context data for the set of answer categories. The context data may be textual, audio, video, or other content that indicates a relative importance of the first answer category in relation to the other answer categories of the set of answer categories or the answer sequence as a whole. The context data may be collected from a corpus of data such as a digital encyclopedia, journal articles, research results, studies, and the like. The context data may be evaluated using a natural language processing technique configured to parse semantic and syntactic content of the context data. At block 1924, aspects of the present disclosure are directed toward determining whether the context data achieves a satisfaction criterion. The satisfaction criterion may be a standard or benchmark to gauge the relative quality or relevance of the collected context data.

As described herein, in response to determining that the context data achieves the satisfaction criterion, the third evaluation rule may be selected at block 1926. Aspects of the third evaluation rule may be directed toward assigning weighting values to each answer category of the answer sequence, and calculating an aggregate score for the answer sequence using the weighting values. Accordingly, at block 1928, the third evaluation rule may be applied and weighting values may be assigned to each answer category based on the context data collected at block 1922.

At block 1930, aspects of the present disclosure are directed toward adjusting the weighting value assigned to each answer category of the answer sequence. In certain embodiments, adjusting the weighting value assigned to each category may include receiving a first set of answer preference data from a user. The answer preference data may indicate an inclination or a disinclination (e.g., of a user) for a particular answer or answer category of the answer sequence. Accordingly, based on the first set of answer preference data, at block 1930 the weighting values assigned to the answer categories may be adjusted. For instance, consider an example related to cancer treatment, in which an individual has a strong objection to chemotherapy. Accordingly, the weighting value assigned to the answer category of chemotherapy may be decreased. Similarly, for an example related to investment options, an individual may have a strong predilection for long-term savings. Accordingly, the weighting value assigned to an answer category of "savings bonds" may be increased. Other methods of adjusting the weighting values are also possible.

At block 1932, aspects of the present disclosure are directed toward assigning a sequence evaluation score to an answer sequence. As described herein, the sequence evaluation score may be the first score identified at block 1914 based on the first evaluation rule, the aggregate score calculated at block 1918 based on the second evaluation rule, calculated at block 1932 using the weighting values assigned based on the third evaluation rule, or generated using another method. As described herein, the sequence evaluation score may represent an overall assessment of the reliability or confidence of the first answer sequence.

In certain embodiments, at block 1932, aspects of the present disclosure are directed toward modifying the sequence evaluation score of a first answer sequence based on a comparison with a second answer sequence. Put differently, the reliability of an answer sequence may be judged relative to the contents of other answer sequences (e.g., an answer sequence that fails to include an important answer category may be penalized.) Accordingly, in certain embodiments, aspects of the present disclosure are directed toward comparing an answer sequence (e.g., a first answer sequence) with another answer sequence (e.g., a second answer sequence), and identifying a first answer category that belongs to the first answer sequence but is absent from the second answer sequence. In response to identifying the first answer category, it may be determined that a first score coupled with a first answer of the first category achieves a first influence threshold. Generally, the first influence threshold may be a quantitative indication of the degree to which the first answer category impacts the sequence evaluation score. In response to determining that the first score achieves the first influence threshold, the sequence evaluation score of the second answer sequence may be modified. Modifying the sequence evaluation score of the second answer sequence may include increasing, decreasing, or otherwise adjusting the sequence evaluation score of the second answer sequence.

For instance, consider once more the example above pertaining to raising a bonsai tree. As described herein, a first answer sequence may include answer categories of "Potting," "Choosing a Location," "Watering," and "Feeding." A second answer sequence may include answer categories of "Potting," "Choosing a Location," and "Feeding." Accordingly, aspects of the present disclosure are directed toward comparing the first answer sequence with the second answer sequence, and determining that the answer category of "Watering" is included in the first answer sequence but not the second answer sequence. Further, the identified answer category may be evaluated to determine whether a first score coupled with a first answer achieves a first influence threshold. In certain embodiments, the first influence threshold may be 85. Accordingly, an answer of "Water when the top centimeter of soil is dry" with a first score of 89 may be determined to achieve the influence threshold. As the second answer sequence does not include the answer category of "Watering," which includes a substantially significant answer, the sequence evaluation score of the second answer sequence may be decreased. In certain embodiments, the magnitude of the decrease may be proportional to the first score of the first answer (e.g., the greater the significance of the missing answer, the greater the second answer sequence is penalized.) In certain embodiments, aspects of the present disclosure are directed toward using a placeholder null value (e.g., 0) in place of the missing answer category during calculation of the sequence evaluation score. Other methods of modifying the sequence evaluation score of the second answer sequence are also possible.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer implemented method for evaluating an answer sequence comprising:
   receiving, by a question-answering system and via a graphical user interface, an input query from a user;
   parsing, using natural language processing techniques configured to parse semantic and syntactic content and by the question-answering system, the input query;
   searching, based on the parsed input query and by the question-answering system, a set of corpora;
   generating, based on the searching and by the question-answering system, a set of answer sequences including a first answer sequence having a first set of answers and a set of scores coupled with the first set of answers;
   identifying, by the question-answering system, a set of answer categories corresponding to the first set of answers of the first answer sequence;
   collecting, by the question-answering system and for the set of answer categories corresponding to the first set of answers of the first answer sequence, context data from the set of corpora indicating a relative importance of a first answer category of the set of answer categories to the first answer sequence;
   determining, by the question-answering system and based on a subject matter corresponding to the first answer sequence, a set of evaluation rules, wherein a first evaluation rule of the set of evaluation rules comprises:
      assigning, based on the context data, a first weighting value to the first answer category of the set of answer categories;
      assigning, based on the context data, a second weighting value to a second answer category of the set of answer categories; and
      calculating, by a statistical algorithm using the first weighting value and the second weighting value, an aggregate score;
   receiving, by the question-answering system and from the user, a first set of answer preference data indicating an inclination for the first answer category of the set of answer categories;

increasing, by the question-answering system and based on the first set of answer preference data, the first weighting value assigned to the first answer category;

generating, by the question-answering system and based on the set of scores and the set of evaluation rules, a first sequence evaluation score for the first answer sequence, wherein generating the first sequence evaluation score for the first answer sequence includes assigning, to the first answer sequence, the aggregate score as the first sequence evaluation score;

comparing, by the question-answering system, the first sequence evaluation score to sequence evaluation scores of other answer sequences of the set of answer sequences; and providing, by the question-answering system and based on the comparing the sequence evaluation scores, the first answer sequence to the user, via the graphical user interface, as a response to the input query.

2. The method of claim 1, further comprising:
receiving, from the user, a second set of answer preference data indicating a disinclination for the second answer category of the set of answer categories; and
decreasing, based on the second set of answer preference data, the second weighting value assigned to the second answer category.

3. A computer implemented method for evaluating an answer sequence comprising:
receiving, by a question-answering system and via a graphical user interface, an input query from a user;
parsing, using natural language processing techniques configured to parse semantic and syntactic content and by the question-answering system, the input query;
searching, based on the parsed input query and by the question-answering system, a set of corpora;
generating, based on the searching and by the question-answering system, a set of answer sequences including a first answer sequence having a first set of answers and a set of scores coupled with the first set of answers;
identifying, by the question-answering system, a set of answer categories corresponding to the first set of answers of the first answer sequence;
collecting, by the question-answering system and for the set of answer categories corresponding to the first set of answers of the first answer sequence, context data from the set of corpora indicating a relative importance of a first answer category of the set of answer categories to the first answer sequence;
determining, by the question-answering system and based on a subject matter corresponding to the first answer sequence, a set of evaluation rules, wherein a first evaluation rule of the set of evaluation rules comprises:
assigning, based on the context data, a first weighting value to the first answer category of the set of answer categories;
assigning, based on the context data, a second weighting value to a second answer category of the set of answer categories; and
calculating, by a statistical algorithm using the first weighting value and the second weighting value, an aggregate score;
receiving, by the question-answering system and from the user, a first set of answer preference data indicating a disinclination for the first answer category of the set of answer categories;
decreasing, by the question-answering system and based on the first set of answer preference data, the first weighting value assigned to the first answer category;
generating, by the question-answering system and based on the set of scores and the set of evaluation rules, a first sequence evaluation score for the first answer sequence, wherein generating the first sequence evaluation score for the first answer sequence includes assigning, to the first answer sequence, the aggregate score as the first sequence evaluation score;
comparing, by the question-answering system, the first sequence evaluation score to sequence evaluation scores of other answer sequences of the set of answer sequences; and
providing, by the question-answering system and based on the comparing the sequence evaluation scores, the first answer sequence to the user, via the graphical user interface, as a response to the input query.

* * * * *